US011162063B2

(12) United States Patent
Cox, Jr. et al.

(10) Patent No.: US 11,162,063 B2
(45) Date of Patent: Nov. 2, 2021

(54) METHODS AND APPARATUS FOR CONDITIONING CELL POPULATIONS FOR CELL THERAPIES

(71) Applicant: THE BOARD OF REGENTS OF THE UNIVERSITY OF TEXAS SYSTEM, Austin, TX (US)

(72) Inventors: Charles S. Cox, Jr., Houston, TX (US);
Brijesh S. Gill, Houston, TX (US);
Kevin Aroom, Houston, TX (US);
Pamela Wenzel, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/855,831

(22) Filed: Apr. 22, 2020

(65) Prior Publication Data
US 2020/0248128 A1      Aug. 6, 2020

Related U.S. Application Data

(62) Division of application No. 15/738,257, filed as application No. PCT/US2016/039044 on Jun. 23, 2016, now Pat. No. 10,669,516.
(Continued)

(51) Int. Cl.
*C12M 1/42* (2006.01)
*C12M 1/12* (2006.01)
(Continued)

(52) U.S. Cl.
CPC .............. *C12M 35/04* (2013.01); *A61K 35/28* (2013.01); *A61P 25/00* (2018.01); *C12M 23/04* (2013.01); *C12M 23/38* (2013.01); *C12M 23/40* (2013.01); *C12M 23/44* (2013.01); *C12M 29/00* (2013.01); *C12N 5/0663* (2013.01); *C12N 2501/02* (2013.01); *C12N 2501/2301* (2013.01); *C12N 2501/24* (2013.01); *C12N 2501/25* (2013.01); *C12N 2501/90* (2013.01); *C12N 2501/999* (2013.01); *C12N 2527/00* (2013.01)

(58) Field of Classification Search
None
See application file for complete search history.

(56) References Cited

U.S. PATENT DOCUMENTS

| 4,323,455 A | 4/1982 | Tanaka et al. |
| 4,661,458 A | 4/1987 | Berry et al. |
| (Continued) | | |

FOREIGN PATENT DOCUMENTS

| CN | 103764813 | 4/2014 |
| EP | 0 419 234 A2 | 3/1991 |
| (Continued) | | |

OTHER PUBLICATIONS

Office Communication issued in Chinese Application No. 201680042078.7, dated Nov. 9, 2020. English translation appended.
(Continued)

*Primary Examiner* — William H. Beisner
(74) *Attorney, Agent, or Firm* — Parker Highlander PLLC

(57) ABSTRACT

A bioreactor system for conditioning of pluripotent cells or cell media is provided. In further aspects, conditioned pluripotent cells and methods for making such cells are provided.

12 Claims, 12 Drawing Sheets

Related U.S. Application Data

(60) Provisional application No. 62/183,273, filed on Jun. 23, 2015.

(51) Int. Cl.
| | |
|---|---|
| *C12M 1/00* | (2006.01) |
| *C12M 3/00* | (2006.01) |
| *A61K 35/28* | (2015.01) |
| *C12N 5/0775* | (2010.01) |
| *A61P 25/00* | (2006.01) |

(56) References Cited

U.S. PATENT DOCUMENTS

| | | | |
|---|---|---|---|
| 5,240,854 | A | 8/1993 | Berry et al. |
| 5,416,022 | A | 5/1995 | Amiot |
| 5,928,945 | A | 7/1999 | Seliktar et al. |
| 6,015,590 | A | 1/2000 | Suntola et al. |
| 6,228,607 | B1 | 5/2001 | Kersten et al. |
| 6,562,616 | B1 | 5/2003 | Toner et al. |
| 7,416,884 | B2 | 8/2008 | Gemmiti et al. |
| 10,669,516 | B2 | 6/2020 | Cox, Jr. et al. |
| 2008/0057571 | A1 | 3/2008 | Loboa et al. |
| 2011/0124078 | A1 | 5/2011 | Edwards et al. |
| 2014/0120608 | A1 | 5/2014 | Carter et al. |
| 2014/0287451 | A1 | 9/2014 | McFetridge |

FOREIGN PATENT DOCUMENTS

| | | |
|---|---|---|
| JP | 5-501953 | 4/1993 |
| RU | 2164240 | 3/2001 |
| WO | WO 1992/005243 | 4/1992 |
| WO | WO 1998/030679 | 7/1998 |
| WO | WO 2004/076608 | 9/2004 |
| WO | WO 2010/148275 | 12/2010 |
| WO | WO 2012/174445 | 12/2012 |
| WO | WO 2013/086284 | 6/2013 |
| WO | WO 2013/192221 | 12/2013 |

OTHER PUBLICATIONS

Extended European Search Report issued in European Application No. 16815316.1, dated Jan. 18, 2019.

International Preliminary Report on Patentability issued in International Application No. PCT/US16/39044, dated Jan. 4, 2018.

International Search Report and Written Opinion issued in International Application No. PCT/US16/39044, dated Nov. 3, 2016.

Office Communication issued in Japanese Application No. 2017-566351, dated Mar. 2, 2020. English Translation.

Office Communication issued in Russian Application No. 2018102213, dated May 15, 2020. English translation appended.

Thin Luu, N., et al. "Crosstalk between mesenchymal stem cells and endothelial cells leads to downregulation of cytokine-induced leukocyte recruitment." *Stem Cells* 31.12 (2013): 2690-2702.

Wagner, Joseph, et al. "Optimizing mesenchymal stem cell-based therapeutics." *Current opinion in biotechnology* 20.5 (2009): 531-536.

Wang, H., et al. "Shear stress induces endothelial differentiation from mouse embiyo mesenchyrnal progenitor cells." *Journal of Surgical Research* 121.2 (2004): 274.

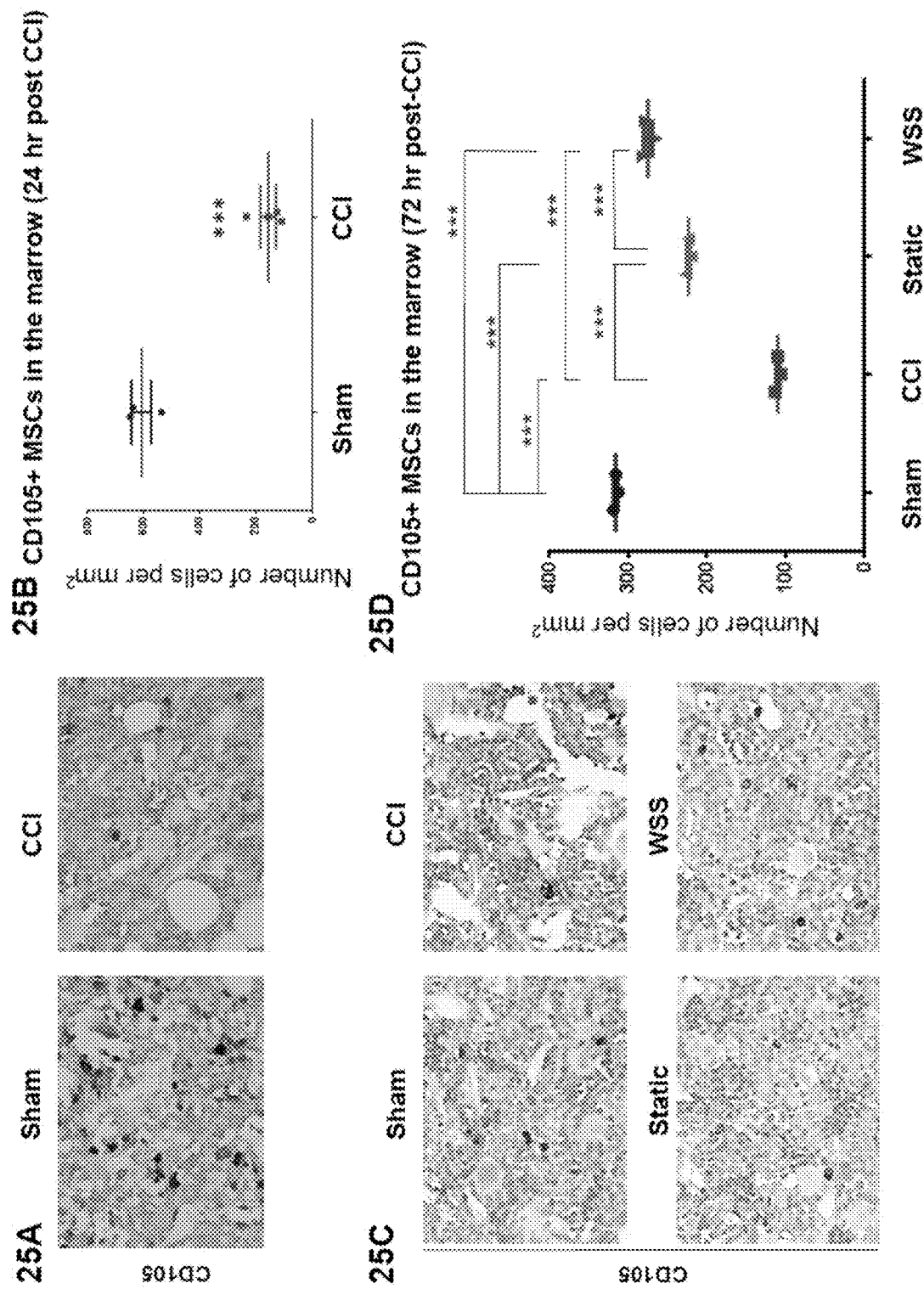
FIGS. 25A-D

METHODS AND APPARATUS FOR CONDITIONING CELL POPULATIONS FOR CELL THERAPIES

This application is a divisional of U.S. patent application Ser. No. 15/738,257, filed Dec. 20, 2017, as a national phase application under 35 U.S.C. § 371 of International Application No. PCT/US2016/039044, filed Jun. 23, 2016, which claims the benefit of U.S. Provisional Patent Application No. 62/183,273, filed Jun. 23, 2015, the entirety of which is incorporated herein by reference.

BACKGROUND OF THE INVENTION

Field of the Invention

Embodiments of the present invention relate to methods and apparatus for conditioning cell populations for improved characteristics for use as therapeutic agents. More specifically, the embodiments of the present invention relate to an apparatus and a method for conditioning stem cells by imposing a controlled shear stress on stem cells disposed along a boundary of a flow chamber in which the stem cells are disposed.

Background of the Related Art

Lineage specific differentiated cell populations are contemplated for use in cell replacement therapies for patients with diseases or disorders. Cell populations that retain the ability to differentiate into specialized cell types (stem cells) and/or secrete certain factors have been contemplated for use in cell-based therapies for patients with a variety of diseases or disorders.

Research and technological developments relating to directed differentiation of stem cells has been postulated to provide treatments for many diseases and disorders. However, there is still a need for the ability to obtain sufficient donor cell populations that are reliably conditioned such that they are predictable in their therapeutic activity. The present methods and apparatus provide a solution to these problems and thus facilitate the use of cells as cellular therapeutics or as the source of soluble factors.

A bioreactor is a device in which components of biological materials, such as stem cell-containing fluids, may be conditioned by manipulation of the factors that influence the materials. The condition of a stem cell-containing fluid is influenced by multiple factors including pH, waste content, nutrient content and the type and concentration of dissolved gases such as, for example, oxygen. These factors may generally be referred to as chemical factors that influence the condition of stem cells in a stem cell-containing fluid.

A bioreactor may enable the manipulation of the condition of the stem cell-containing fluids by control of non-chemical factors. Conventional apparatuses and methods of conditioning cell populations for conventional cell therapies fail to enable the precise control of mechanical shear to the cells to be conditioned. Apparatus and methods for controllably applying shear stress to cells to be conditioned within a bioreactor flow chamber capable of large-scale cell production are therefore desired.

SUMMARY OF THE INVENTION

Embodiments of the present invention include apparatus that enable the control of at least one mechanical factor that influences the condition of the stem-cell containing fluids. More specifically, embodiments of the present invention include apparatus that enable the control of the rate of shear stress applied to stem cells within the stem cell-containing fluid.

Embodiments of the present invention may be used to flow a media fluid through one or more flow chambers shaped to provide a very high flow boundary layer perimeter to cross-sectional flow area ratio to thereby maximize the conditioning effects of mechanical forces (shear) on stem cells adherent to the chambers.

The very high boundary layer perimeter for a corresponding cross-sectional flow area is calculated, for a given flow passage, as the perimeter of the flow chamber divided by the cross-sectional flow area. For example, a circular flow passage provides the minimum achievable flow boundary layer perimeter for a corresponding cross-sectional flow area, which is calculated as: $2\pi r \div \pi r^2 = 2/r$. It will follow that a flow passage having a minimal perimeter to cross-sectional flow area ratio generally provides for minimal shear stress imparted to the fluid as it flows through the flow passage, all other factors (turbulent or laminar flow regime, surface roughness, etc.) being the same.

The maximum flow boundary layer perimeter for a corresponding cross-sectional flow area is provided by, for example, an infinitely wide and infinitesimally thin passage, for which the achievable flow boundary layer perimeter for a corresponding cross-sectional flow area theoretically approaches ∞. Of course, an infinitely wide and infinitesimally narrow passage is impractical as it would impose infinite resistance to flow, but a very high flow boundary layer perimeter for a corresponding cross-sectional flow area is achieved by providing wide, but thin flow passages to promote the application of shear along the flow boundary layer perimeter to a stem cell-containing fluid moved therethrough.

One embodiment of an apparatus of the present invention provides an apparatus, comprising a first cap having a first end, a second end, a wall therebetween, an inlet fluid connector proximal to the first end, a riser bore proximal to the first end, and feed passage extending from the inlet fluid connector to the riser bore to dispose the riser bore in fluid communication with the inlet fluid connector, a second cap having a first end, a second end, a wall therebetween, an outlet fluid connector proximal to the second end, a riser bore proximal to the second end, and a drain passage extending from riser bore to the outlet fluid connector to dispose the riser bore in fluid communication with the outlet fluid connector, and at least one intermediate module disposed intermediate the wall of the first cap and the wall of the second cap and in sealed engagement with each of the first cap and the second cap upon assembly of the apparatus, each intermediate module including a frame having a first end, a second end, a barrier therebetween having a first side disposed toward the wall of the first cap and a second side disposed toward the wall of the second cap, the barrier disposed within the frame and between the first end and the second end to form a first flow chamber between the wall of the first cap and the barrier of the intermediate module upon sealable engagement of a sealing face of the first cap with a sealing face of a first side of the intermediate module and to also form a second flow chamber between the wall of the second cap and the barrier of the intermediate module upon sealable engagement of a sealing face of the second cap with a sealing face of a second side of the intermediate module with a sealing face of the second cap with the intermediate module, a module feed bore in the frame proximal to the first end of the intermediate module for sealably engaging the riser bore of the first cap upon assembly of the apparatus, a distribution channel in the frame proximal to the first end of the intermediate module and in fluid communication with the module feed bore for distributing a fluid flow received into the distribution channel from the module feed bore, a plurality of flow chamber feed ports disposed proximal to the first end of the intermediate module and in fluid communication with the distribution channel for introducing a fluid flow received into the first and second flow chambers, a plurality of flow chamber drain ports disposed proximal to the second end of the intermediate module and in fluid communication with the first and second flow chambers, a gathering channel disposed along the second end of the intermediate module and in fluid communication with the first and second flow chambers through the flow chamber drain ports, a module drain bore proximal to the second end of the intermediate module and in fluid communication with the gathering channel and for sealably engaging the riser bore of the second cap upon assembly of the apparatus, wherein upon assembly of the apparatus with the one or more intermediate modules disposed intermediate the first cap and the second cap to sealably engage the first side sealing surface on the one or more intermediate modules with the sealing surface on the first cap and to also sealably engage the second side sealing surface on the one or more intermediate modules with the sealing surface on the second cap disposes the inlet fluid connector of the first cap in sealed engagement with the outlet fluid connector on the second cap to provide a bifurcated fluid path that includes the first flow chamber, disposed intermediate the at least some of the plurality of flow chamber feed ports and at least some of the plurality of flow chamber drain ports and intermediate the at least one intermediate module first side and the first cap, and a second flow chamber, disposed intermediate the at least some of the plurality of flow chamber feed ports and at least some of the plurality of flow chamber drain ports and intermediate the at least one intermediate module second side and the second cap, wherein the plurality of flow chamber feed ports distributed along the distribution channel and the plurality of flow chamber drain ports distributed along the gathering channel of the intermediate module provide for a more uniform localized fluid velocity within the flow chambers upon providing a fluid pressure differential across the inlet fluid connector and the outlet fluid connector of the apparatus, wherein a ratio of the perimeter of the first flow chamber to the cross-sectional flow area of the first flow chamber exceeds.

Certain embodiments of the invention concern a method of producing a conditioned composition. As used herein, a conditioned composition refers to a composition that has been subjected to the conditioning effects of mechanical forces. For example, the mechanical force can be an application of controlled shear stress with a force sufficient to produce a conditioned composition. In some aspects, the conditioned composition comprises a population of conditioned pluripotent cells (e.g., MSCs). Thus, certain aspects concern the isolation of a population of conditioned pluripotent cells. In further aspects, the conditioned composition is a media (e.g. a cell-free media) comprising secreted factors from pluripotent cells that have been subjected to a controlled sheer stress.

Aspects of the embodiments involve culturing of the stem cells on a substrate to allow cell adhesion. In some cases, the substrate is a surface that supports the growth of the stem cells in a monolayer. For example, in some aspects, the surface is a plastic or glass surface, such as a surface that has been coated with extracellular matrix materials (e.g., collagen IV, fibronectin, laminin and/or vitronectin). In further aspects, the substrate may be modified to incorporate a surface (or surface coating) with increased or decreased surface energy. Examples of low energy materials that may be used as a surface or surface coating include, without limitation, hydrocarbon polymers, such as polyethylene, or polypropylene and nitrides. For instance, a surface or surface coat may comprise Polyhexafluoropropylene, Polytetrafluoroetylene, Poly(vinylidene fluoride), Poly(chlorotrifluoroethylene), Polyethylene, Polypropylene, Poly (methylmethacrylate)—PMMA, Polystyrene, Polyamide, Nylon-6,6, Poly(vinylchloride), Poly(vinylidene chloride), Poly(ethylene terephthalate), Epoxy (e.g., rubber toughened or amine-cured), Phenol-resorcinol resin, Urea-formaldehyde resin, Styrene-butadiene rubber, Acrylonitrile-butadiene rubber and/or Carbon fibre reinforced plastic. Examples of high energy materials that may be used as a surface or surface coating include, without limitation, metals and oxides. For instance, a surface or surface coat may comprise Aluminium oxide, Berylium oxide, Copper, Graphite, Iron oxide (Fe 2O 3), Lead, Mercury, Mica, Nickel, Platinum, Silicon dioxide—silica and/or Silver.

Further aspects of the embodiments concern the application of controlled shear stress with a force sufficient to produce a conditioned composition. In certain aspects, the shear stress is applied in the form of fluid laminar shear stress. For example, the force of the shear stress is at least about 1, 2, 3, 4, 5, 6, 7, 8, 9 or 10 dynes per square centimeter. In certain instances, the force of the shear stress is at least 5, 10 or 15 dynes per square centimeter, such as between about 5-20; 5-15; 10-20 or 10-15 dynes per square centimeter. In some aspects, the controlled shear stress is applies for a period of between about 1 minute and two days. For example, the controlled shear stress can be applied for a period of between 5 minutes to 24 hours; 10 minutes to 24 hours; 0.5 hours to 24 hours or 1 hour to 8 hours. In further aspects, cells of the embodiments are exposed to an elevated pressure.

In still further aspects, cells or media from a culture of the embodiments are tested periodically to determine the level of conditioning. For example, a sample comprising cells or media can be taken from the culture about every 10 minutes, 15 minutes, 30 minutes or every hour. Such samples may be tested, for example to determine the expression level of anti-inflammatory factors, such as transcription factors or cytokines. In particular aspects, cells or media can be taken from a sampling port positioned in a location of lower fluid pressure, including for example near the inlet of a pump configured to direct fluid through the apparatus.

In certain aspects, a starting population of stem cells is obtained. For example, the starting stem cell population can comprise induced pluripotent stem (iPS) cells or mesenchymal stem cells (MSCs). In some aspects, the MSCs are isolated from tissue. For example, in some aspects, the tissue comprises bone marrow, cord blood, peripheral blood, fallopian tube, fetal liver, lung, dental pulp, placenta, adipose tissue, or amniotic fluid. In further aspects the cells are human cells. For example, the cells can be autologous stem cells. In some aspects, the stem cells are transgenic cells.

In further aspects of the embodiments, a method of producing a conditioned composition comprises passing fluid over the stem cells for the application of controlled shear stress. For example, the fluid passed over the stem cells can be a cellular growth medium. In some aspects, the growth medium comprises at least a first exogenous cytokine, growth factor, TLR agonist or stimulator of inflammation. For example, the growth medium can comprise IL1B, TNF-α, IFNγ, PolyI:C, lipopolysaccharide (LPS), phorbol myristate acetate (PMA) and/or a prostaglandin. In certain specific aspects, the prostaglandin is 16,16'-dimethyl prostaglandin E2 (dmPGE2).

In certain aspects, conditioned stem cells of the embodiments have at least 2-, 3-. 4-. 5- or 6-fold higher expression of an anti-inflammatory gene compared to the starting populating of stem cells. For example, the anti-inflammatory gene can be TSG-6, PGE-2, COX-2, IL1Ra, HMOX-1, LIF, and/or KLF2.

In further embodiments, the conditioned composition comprises a conditioned media composition. Thus, certain aspects concern the isolation of conditioned media after the application of shear stress. In some cases, the conditioned media is essentially free of cells.

Further aspects of the embodiments concern the application of shear stress in a bioreactor (e.g., such as a bioreactor detailed herein). In certain aspects, the bioreactor system comprises an inlet fluid feed plate, a base plate, and a plurality of intermediate plates positioned between the inlet fluid feed plate and the base plate. For example, the intermediate plate comprises a first end, a second end, a first side, and a second side; a distribution channel proximal to the first end; and a gathering channel proximal to the second end. In further aspects, the distribution channel extends between the first side and the second side of the intermediate plate. In certain aspects, the gathering channel extends between the first side and the second side of the intermediate plate. In some cases, the bioreactor system further comprises a reservoir, a first conduit, and a second conduit. In certain aspects, the inlet fluid feed plate comprises a first fluid inlet, a first fluid outlet, a second fluid inlet and a second fluid outlet. For example, the reservoir is coupled to the first fluid inlet via the first conduit and is coupled to the second fluid outlet via the second conduit.

In further aspects of the embodiments, the bioreactor system comprises a pump coupled to the first fluid outlet and the second fluid inlet of the inlet fluid feed plate. In certain aspects, the pump is configured to draw a fluid from the reservoir through first fluid inlet and the first fluid outlet and to direct the fluid through the second fluid inlet, across a plurality of intermediated plates, out the second inlet, and back to the reservoir. In some aspects, a velocity of the fluid through the second fluid inlet is controlled by a rotational speed of the rolling element of the pump. In certain aspects, the bioreactor system provides a high-flow boundary layer perimeter to cross-sectional flow area ratio. In some aspects, the bioreactor system is capable of large-scale cell production. For example, the method of producing a conditioned composition is automated.

Certain aspects of the embodiments provide a composition of a therapeutically effective amount of conditioned stem cells. Some aspects provide a method of treating a subject in need of such treatment comprising administering a therapeutically effective amount of conditioned stem cells. For example, the cells can comprise a conditioned composition (e.g., a cell composition or conditioned media) obtained by a method in accordance with the embodiments. As demonstrated herein such conditioned compositions can, in some aspects, provide for enhanced engraftment of stem cells in a subject. For example, in some aspects, the subject has chronic or acute inflammation, graft-versus-host disease, a neurological injury (e.g., an ischemic injury, such as stroke, or a traumatic brain injury), musculoskeletal trauma, or an autoimmune disorder. In some aspects, the conditioned stem cells are administered in combination with one or more additional therapeutic agents.

In still a further embodiment there is provided a method of increasing CD105$^+$ cells in the bone marrow of a patent comprising administering an effective amount of stem cells (e.g., mesenchymal stem cells) to the patient. For example, the cells can comprise a conditioned composition (e.g., a cell composition or conditioned media) obtained by a method in accordance with the embodiments. In some aspects, the patient has a neurological injury, such as an ischemic injury (e.g., from a stroke) or a traumatic brain injury. In certain aspects, the patient has suffered from the neurological injury less than 24, 18, 12 or 6 hours before the administration of the cells.

Certain aspects, the embodiments concern administration of cells and/or conditioned compositions. In some aspects, the administration can be local, such as in or adjacent to, diseased or damaged tissues. In further aspects, the administration is systemic. For example, the administration can be by injection of a composition, such as intravenous injection.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The objects and advantages of the present methods, system and apparatus will be better understood and more readily apparent when considered in conjunction with the following detailed description and accompanying drawings which illustrate, by way of example, preferred embodiments of this system and methods.

FIGS. 25A-D illustrate that disruption in cellular composition of bone marrow caused by traumatic brain injury in rats is abrogated by intravenous administration of WSS-preconditioned human MSCs. (A) Immunodetection of endogenous rat MSCs in the bone marrow 24 hours after traumatic brain injury by CCI reveals depletion of the CD105$^+$ population (counterstain is derived from nuclear fast red). (B) Fewer CD105$^+$ MSCs are present in the bone marrow following CCI. (C) CD105 is detected at 72 hours after injury (hematoxylin counterstain). (D) Quantification of CD105 MSC frequency at 72 hours after CCI reveals protection of bone marrow cellular composition by MSC therapy when administered intravenously at 24 hours post-CCI. The protective effects on the CD105$^+$ MSC population are enhanced by WSS preconditioning of MSCs used therapeutically (One-way ANOVA, ** *p<0.001).

DETAILED DESCRIPTION

Figure 1:
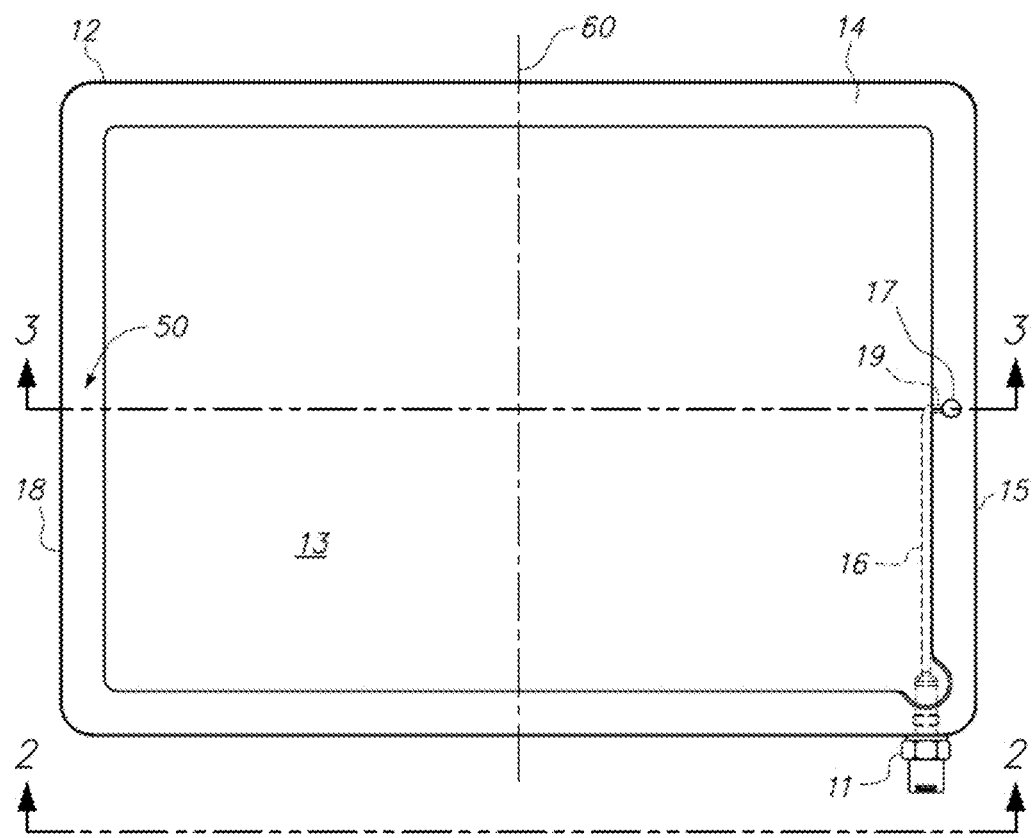
FIG. 1 is a plan view of a feed cap of the bioreactor case according to the present disclosure.

When dealing with multipotent stem cells, such as mesenchymal stem cells (MSCs), controlling the outcome of differentiation is a critical step in developing cellular therapies. Generating consistent results requires precise control of the cell's environment, which includes a number of parameters. These include chemical factors such as nutrients, waste products, pH and dissolved gases. Many state of the art bioreactors have been designed and built to control and monitor these chemical parameters.

However, the mechanical environment also plays a significant role in the outcome of a stem cell. The mechanical environment is dependent upon two major elements: the substrate and the dynamic state of the surrounding media. Substrate stiffness can be controlled through careful selection of surface treatments or coatings, which can influence both the adherence of the cells to the substrate as well as differentiation outcome.

After a population of cells has adhered to a substrate, they are subjected to mechanical forces applied by the media in which the cells are immersed. In conventional cell culture, these forces are essentially zero since there is no bulk flow of media. Existing bioreactor systems have constant or variable fluid flow (media), but lack design control of the pattern of flow (laminar-uni or bi-directional vs. turbulent) or the degree of shear forces that interact with the cells. Moving fluid exerts on cells a shear stress that is proportional to the fluid velocity and viscosity. Most mechanotransduction studies have been performed in the laminar flow regime where shear stress behavior is well known and characterized by simple equations. Laminar flow is characterized by a non-uniform velocity profile across the cross-section of the flow channel. Fluid velocity at the boundaries (e.g. walls) can be assumed to be zero, known as the "no-slip condition" or "boundary condition." A straightforward equation describing shear stress (τ) for Newtonian fluids in laminar flow is $\tau = -\mu \, (du/dy)$, where µ is viscosity and u is velocity of the fluid at a particular depth in the channel. Knowing media viscosity and fluid velocity, applied shear stress can be calculated.

Cell populations that retain the ability to differentiate into multiple cell types (e.g., stem cells) have proven useful for developing large numbers of lineage specific differentiated cell populations. Mesenchymal stem cells (MSCs) are one such type of stem cell and are known for being both multipotent and self-renewing. MSCs have thus emerged as candidate cellular therapeutics and can potentially provide a sustained source of bioactive immunomodulatory molecules. However, presently one of the obstacles limiting clinical efficacy of use of MSC is that the induction of MSC function is heavily dependent upon the presence of cytokines and signals produced by activated immune cells that in turn initiate the immunomodulatory activities of MSC. Prior to the present methods, for example, this variability has translated into unpredictable therapeutic activity of stem cell compositions.

In some aspects, a bioreactor system described herein provides increased numbers of stem cells (e.g., MSCs), which have also been predictably and reliably conditioned in vitro with regards to immunomodulatory function. Stem cells, thus obtained, provide therapeutically effective numbers of MSC which are reliably and consistently conditioned with regards to immunomodulatory function. In other embodiments, the system provides a source of secreted factors which can be isolated and purified for use as therapeutics.

In some embodiments, such methods can provide conditioned cells, such as MSC, for use in therapy and, for example, suppression of chronic or acute inflammation associated with injury (e.g., neurological injury), graft-versus-host disease, and autoimmunity. Such conditioned composition have been demonstrated herein to provide enhance engraftment potential for cells upon administration, which could significantly enhance the efficacy of therapeutic methods.

Certain embodiments include a system for use in producing increased numbers of therapeutically predictably conditioned cells such as, but not limited to, MSCs for use in cell-based therapies. In some embodiments, the system described can be used for, among other things, conditioning MSCs to exhibit anti-inflammatory and immunomodulatory properties, to treat many types of musculoskeletal trauma and inflammatory conditions when, for example, such conditioned cells or factors they produce are injected at the site of an injury. In some embodiments, this system comprises a modular bioreactor system that integrates control of the hydrodynamic microenvironment to direct mechanical-based conditioning of cells, such as, but not limited to MSC.

A bioreactor case is used to condition cells within a stream of media fluid in accordance with the present invention (e.g., the media is passed over adherent cells to provide an applied shear force). An embodiment of a bioreactor case is illustrated in the appended figures, which are discussed below.

FIG. 1 is a plan view of a feed cap 12 of an embodiment of a bioreactor case. The feed cap 12 comprises a first end 15 and a second end 18 and a wall 13 therebetween. The feed cap 12 further comprises a feed passage 16 (in dotted lines) proximal to the first end 15 and originating at an inlet fluid connector 11 and terminating at a riser bore 17 extending from the feed passage 16 towards the viewer of FIG. 1. A short portion 19 of the feed passage 16 in the embodiment of the feed cap 12 of FIG. 1 is turned perpendicular to the feed passage 16 to connect to the riser bore 17. The feed cap 12 includes a sealing face 14 surrounding the wall 13. It should be noticed that there is no second riser bore on the feed cap 12 at location 50. The reason for noting this absence will become clear after consideration of the disclosure that follows.

Figure 2:
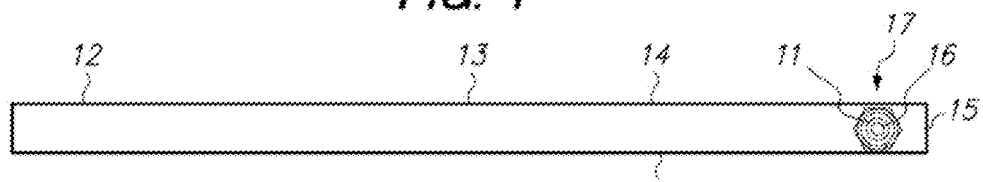
FIG. 2 is a side elevation view of the feed cap of FIG. 1.
Figure 3:
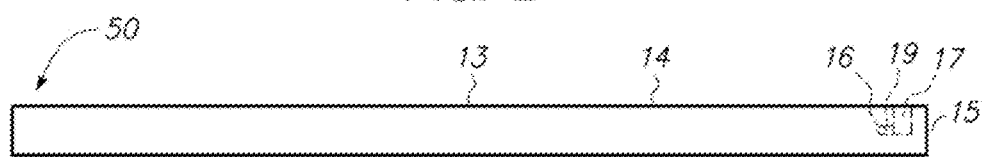
FIG. 3 is a sectional elevation view of the feed cap of FIGS. 1 and 2 taken through the riser bore.

FIG. 2 is a side elevation view of the feed cap 12 of FIG. 1 revealing a seal 16 inside the inlet fluid connector 11 to sealably engage a fluid conduit (not shown) connected to a pressurized source of a fluid. The arrow indicates the location of the riser bore 17 proximal to the first end 15 of the feed cap 12. The wall 13 of the feed cap 12 is illustrated in FIGS. 2 and 3 as being on a top side of the feed cap 12 opposite to the exterior 20 of the feed cap 12 illustrated as being on a bottom side of the feed cap 12. It will be understood that the caps and modules of embodiments of the apparatus of the present invention may be otherwise oriented without impairing the function.

FIG. 3 is a sectional view of the feed cap 12 of FIGS. 1 and 2 taken through the riser bore 17 proximal to the first end 15 of the feed cap 12. The riser bore 17 receives fluid from the feed passage 16 and delivers the fluid flow to one or more intermediate modules (not shown in FIG. 3) at least one of which is sealably received against the sealing face 14.

Figure 4:
FIG. 4 is an end view of the feed cap of FIGS. 1-3.

FIG. 4 is an end view of the feed cap 12 of FIGS. 1-3. FIG. 4 illustrates the location of the inlet fluid connector 11 proximal to the first end 15 of the feed cap 12, the feed passage 16 extending from the inlet fluid connector 11 to the riser bore 17. It should be noted that the inlet fluid connector 11, the feed passage 16 and the riser bore 17 of the feed cap 12 are disposed proximal to the first end 15 of the feed cap 12, and that no corresponding fluid passages are disposed proximal to the second end 18 of the feed cap 12.

Figure 5:
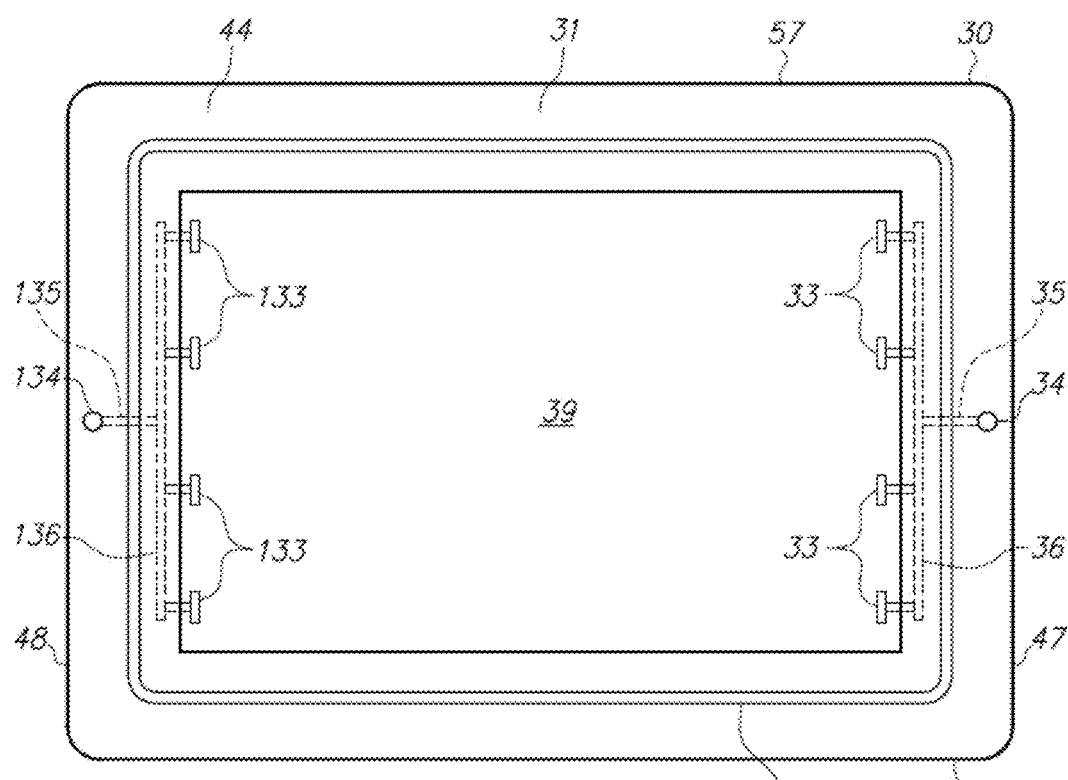
FIG. 5 is a plan view of an intermediate module of the bioreactor case according to the present disclosure.

FIG. 5 is a plan view of an intermediate module 30 of the bioreactor case of the present invention adapted for sealably and operatively engaging the feed cap 12. The intermediate module 30 comprises a first side 31 and a second side 32 (not shown in FIG. 5), each having a sealing face 44 to engage the sealing face 14 of the feed cap 12. The intermediate module 30 further includes a first module bore 34 through the intermediate module 30 and proximal to a first end 47 of the intermediate module 30. The module bore 34 is positioned to meet and to coincide with the riser bore 17 of the feed cap 12 of FIGS. 1-4 upon sealable engagement between the sealing face 44 on the first side 31 of the intermediate module 30 and the corresponding sealing face 14 of the feed cap 12. The intermediate module 30 further includes a second module bore 134 proximal to a second end 48 of the intermediate module 30 and in a position to coincide with and engage a second feed cap 12 (the second feed cap 12 may be identical to the first feed cap 12 but rotated 180 degrees about the axis 60 of FIG. 1. It will be understood that the second feed cap 12 will engage a sealing face 44 on a second side 32 of an intermediate module 30 and the first feed cap 12 will engage a sealing face 44 of the first side 31 of the intermediate module 30. It will further be understood that the absence of a second riser bore 17 proximal to the second end 18 of the feed cap 12 enables the sealing face 14 of the feed cap 12 to seal off the second module bore 134 of the intermediate module 30 that is proximal to the second end 48 of the intermediate module 30. The feed cap 12 may, in one embodiment of the apparatus of the present invention, be thus structured to function, in a first mode in which a feed cap 12 engages the first side 31 of the intermediate module 30, to receive a flow of fluid and deliver the flow to a first end 47 of the intermediate module 30 and, in an inverted second mode in which the second feed cap 112 engages the second side 32 of the intermediate module 30, to receive a flow of fluid from a plurality of fluid chambers including at least a first fluid chamber 38A formed between the wall 13 of the first feed cap 12 and the barrier 39 of the intermediate module 30 upon engagement of the sealing face 14 of the first feed cap 12 with the sealing face 44 of the inverted second feed cap 112, and a second fluid chamber 38B formed between the wall 113 of the inverted second feed cap 112 and the barrier 38 of the intermediate module 30 upon engagement of the sealing face 14 of the second feed cap 112 with the sealing face 114 of the inverted second feed cap 112. The structure of the second feed cap 112 is discussed further in connection with FIGS. 9-12.

The intermediate module 30 of FIG. 5 further includes a diffuser feed channel 35 proximal to the first end 47 of the intermediate module 30 and originating at the module bore 34 and terminating at a distribution channel 36. The diffuser feed channel 35 extends generally distal to the first module bore 34 proximal to the first end 47 of the intermediate module 30 to the distribution channel 36. The distribution channel 36 of the intermediate module 30 receives a fluid flow from the diffuser feed channel 35 and extends from the diffuser channel 35 towards a first edge 57 of the intermediate module 30 and also from the diffuser channel 35 towards a second edge 58 of the intermediate module 30. Similarly, the intermediate module 30 of FIG. 5 further includes an infuser drain channel 135 proximal to the second end 48 of the intermediate module 30 and originating at the infusers 133 and terminating at the gathering channel 136. The infuser drain channel 135 extends generally proximal to the second module bore 134 proximal to the second end 48 of the intermediate module 30 to the gathering channel 136. The gathering channel 136 of the intermediate module 30 receives a fluid flow from the infusers 133 and directs the fluid flow to the second module bore 134 through the infuser drain channel 135.

Figure 6:
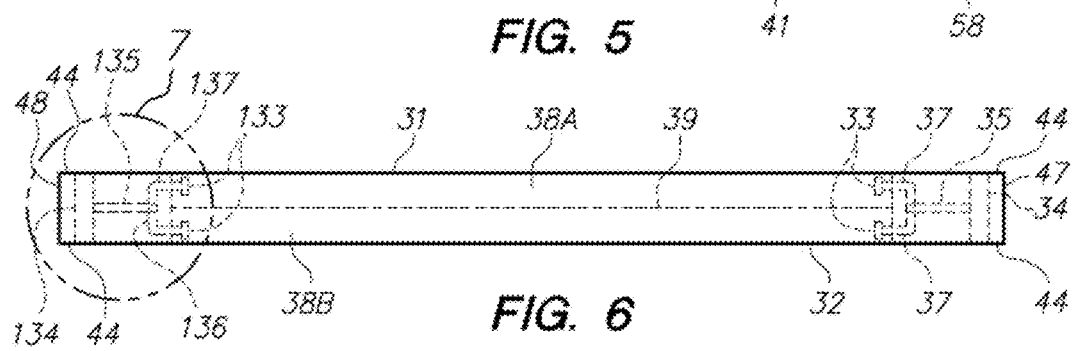
FIG. 6 is a side elevation view of the intermediate module of FIG. 5.

FIG. 6 is a side elevation view of the intermediate module 30 of FIG. 5 revealing the positioning of a plurality of fluid diffusers 33 disposed within the first fluid chamber 38A, a plurality of fluid diffusers 33 disposed within the second fluid chamber 38B, a plurality of fluid infusers 133 disposed within the first fluid chamber 38A and a plurality of fluid infusers 133 disposed within the second fluid chamber 38B, the pluralities of fluid diffusers 33 being proximal to a first end 47 of the intermediate module 30 and the pluralities of fluid infusers 133 being proximal to the second end 48 of the intermediate module 30. It will be understood that the term "diffuser," as used herein, means a device for reducing the velocity and increasing the static pressure of a fluid. It will be understood that the term "infuser," as used herein, means a device for receiving a low velocity, high pressure flow and converting into a higher velocity, lower pressure flow.

Figure 7:
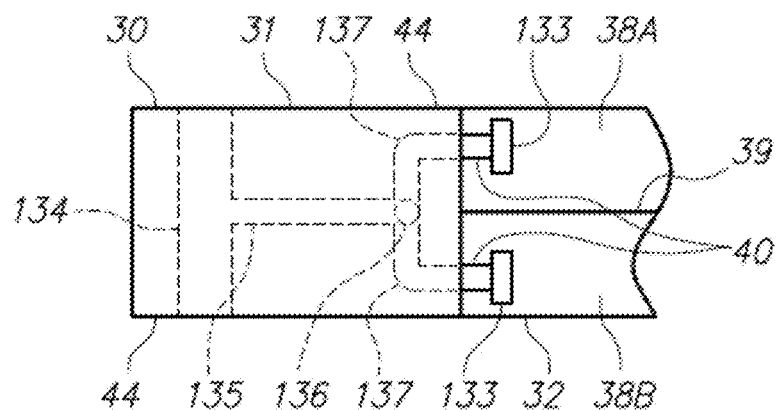
FIG. 7 is an enlarged view of the fluid passages at a second end of the side elevation view of the intermediate module of FIG. 6.

FIG. 7 is an enlarged view of a plurality of connected fluid passages and infusers 133 at a second end 48 of the side elevation view of the intermediate module 30 of FIG. 6. It will be understood that the arrangement of fluid passages in the embodiment of the apparatus of the present invention illustrated in the appended figures can be arranged in different ways without materially altering their function. FIG. 7 reveals an intermediate module 30 having a second module bore 34 therethrough. The second module bore 134 is fluidically connected to a gathering channel 136 through an infuser drain channel 135. The gathering channel 136 extends into the page and out of the page, as seen by the viewer of FIG. 7, to fluidically connect with a plurality of diffusers 133 through a corresponding plurality of port channels 137. The fluid enters the first fluid chamber 38A and the second fluid chamber 38B which are separated one from the other by the barrier 39, to the infusers 133, to the port channels 137, the gathering channel 136, the infuser drain channel 135 to the second module bore 134. It will be noted that FIG. 7 illustrates a portion 40 of the plurality of port channels 137 extend into the first and second fluid chambers 38A and 38B.

Figure 8:
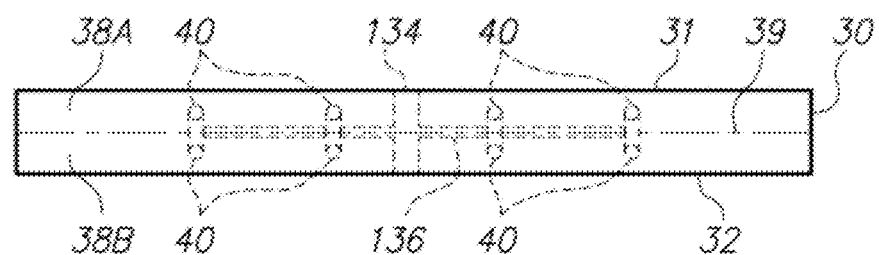
FIG. 8 is an end view of the second end of the intermediate module of FIGS. 5-7.

FIG. 8 is a sectional end view of the intermediate module of FIGS. 5-7 revealing the locations of the infusers 133 that receive flow from the first flow chamber 38A and the second flow chamber 38B. It will be understood that FIG. 8 may also be viewed as a sectional end view of the intermediate module 30 revealing the locations of the diffusers 33 that introduce flow into the first flow chamber 38A and the second flow chamber 38B. FIG. 8 illustrates the spacing of the infusers 133 (at the second end 48 of the intermediate module 30) and of the diffusers 33 (at the first end 47 of the intermediate module 30).

Figure 9:
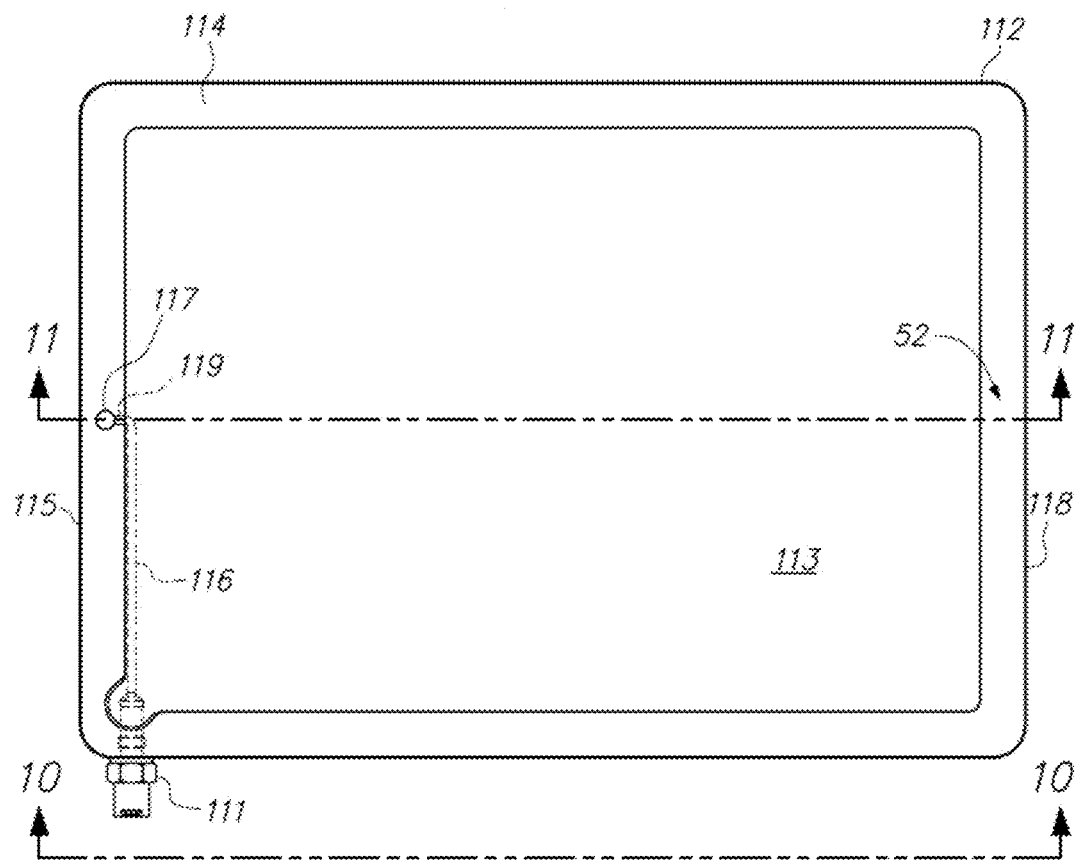
FIG. 9 is a plan view of a drain cap of the bioreactor case of the present invention.

FIG. 9 is a plan view of a drain cap 112 of an embodiment of a bioreactor case of the present invention. The drain cap 112 comprises a first end 115 and a second end 118 and a wall 113 therebetween. The drain cap 112 further comprises a drain passage 116 (in dotted lines) proximal to the first end 115 and originating at a riser bore 117 and terminating at an outlet fluid connector 111. The riser bore 117 extends from the drain passage 116 towards the viewer of FIG. 9. A short portion 119 of the drain passage 116 in the embodiment of the drain cap 112 of FIG. 9 is turned perpendicular to the drain passage 116 to connect to the riser bore 117. The drain cap 112 includes a sealing face 114 surrounding the wall 113.

Figure 10:
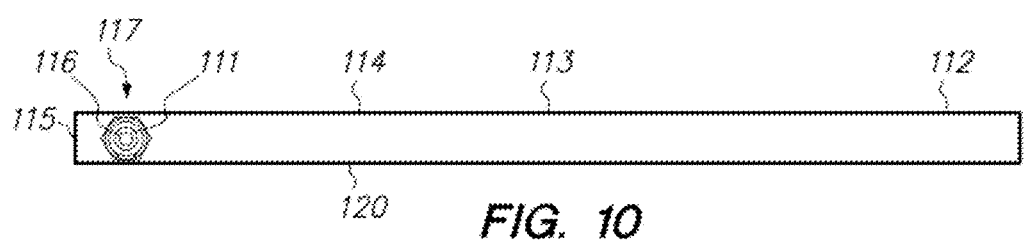
FIG. 10 is a side elevation view of the drain cap of FIG. 10.

FIG. 10 is a side elevation view of the drain cap 112 of FIG. 9 revealing a seal 116 inside the outlet fluid connector 111 to sealably engage a fluid conduit (not shown) connected to a collector to receive a conditioned fluid from the bioreactor 10. The arrow indicates the location of the riser bore 117. The wall 113 of the drain cap 112 is illustrated as being on a top side of the drain cap 112 opposite to the exterior 120 of the drain cap 112 illustrated as being on a bottom side of the drain cap 112. It will be understood that the caps and modules of embodiments of the apparatus of the present invention may be otherwise oriented without impairing the function.

Figure 11:
FIG. 11 is a sectional elevation view of the drain cap of FIGS. 10 and 11 taken through the riser bore.

FIG. 11 is a sectional side view of the drain cap 112 of FIGS. 9 and 10 taken through the riser bore 117. The riser bore 117 receives fluid from the first fluid chamber 38A and the second fluid chamber 38B by way of the second module bore 134 of the intermediate module 30 (see FIGS. 5-8) and delivers the flow to the drain cap 112 having a sealing surface 114 sealably received against the sealing face 44 of the first side 31 of the intermediate module 30.

Figure 12:
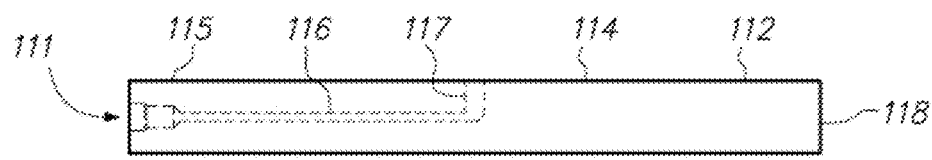
FIG. 12 is an end view of the drain cap of FIGS. 10-12.

FIG. 12 is a sectional end view of the drain cap 112 of FIGS. 9-11. FIG. 12 illustrates the location of the outlet fluid connector 111 proximal to the first end 115 of the drain cap 112, and the drain passage 116 extending from the outlet fluid connector 111 to the riser bore 117. It should be noted that the outlet fluid connector 111, the drain passage 116 and the riser bore 117 of the drain cap 112 are disposed proximal to the first end 115 of the drain cap 112, and that no corresponding fluid passages are disposed proximal to the second end 118.

Figure 13:
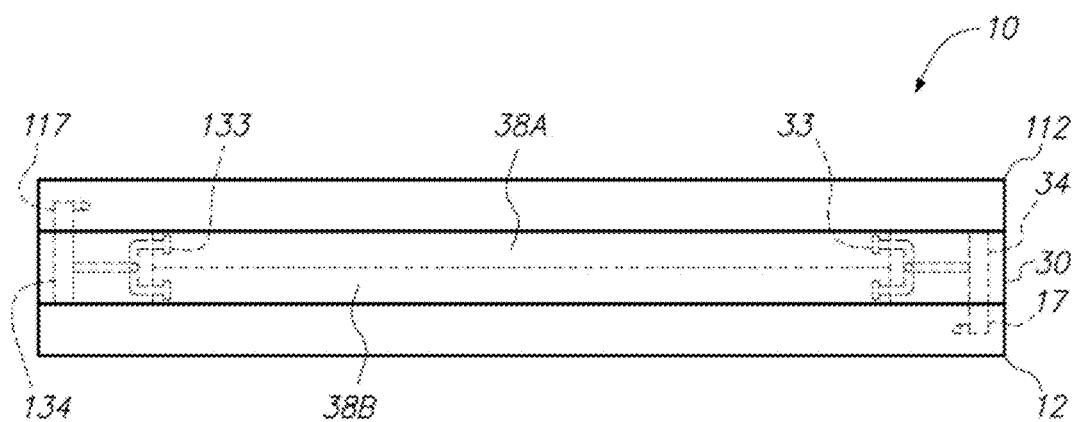
FIG. 13 is a sectional elevation view of an assembled bioreactor case of the present disclosure with a bifurcated fluid path connectable to a vessel (not shown) containing fluid to be conditioned using the bioreactor and connectable to collector vessel (not shown) to receive fluid from the bioreactor.

FIG. 13 is a perspective view of an assembled bioreactor case 10 of the present invention with the inlet fluid connector 11 and the outlet fluid connector 111 of the feed cap 12 and the drain cap 112, respectively, omitted from the FIG. 13 to better reveal the positioning of the riser bore 17 of the feed cap 12, the riser bore 117 of the drain cap 112, the first module bore connectable to a vessel (not shown) containing fluid to be used in conditioning stem cells disposed within the flow chambers 38A and 38B of the bioreactor 10 and an outlet fluid connector 111 (not shown) connectable to a vessel to receive conditioned fluid from the bioreactor.

It will be understood that the assembled bioreactor case 10 illustrated in FIG. 13 comprises a feed cap 12, a drain cap 112 and an intermediate module 30 therebetween. It will be further understood that the rate and direction of flow of a fluid through the bioreactor case 10 depends on the pressure differential (difference between the pressure at the fluid inlet connector 11 and the pressure at the fluid outlet connector 111), the resistance to fluid flow through the bioreactor 10, the viscosity of the fluid and other factors. The feed cap 12, the intermediate module 30 and the drain cap 112 may be secured in the assembled configuration of the bioreactor case 10 of FIG. 13 in various ways including the use of clamps, bands, ties and the like.

Figure 14:
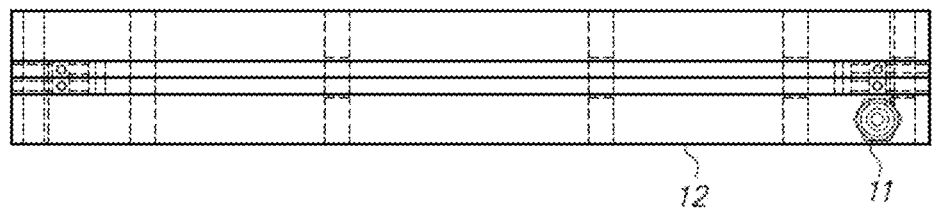
FIG. 14 is a side elevation view of bioreactor case of FIG. 13.
Figure 15:
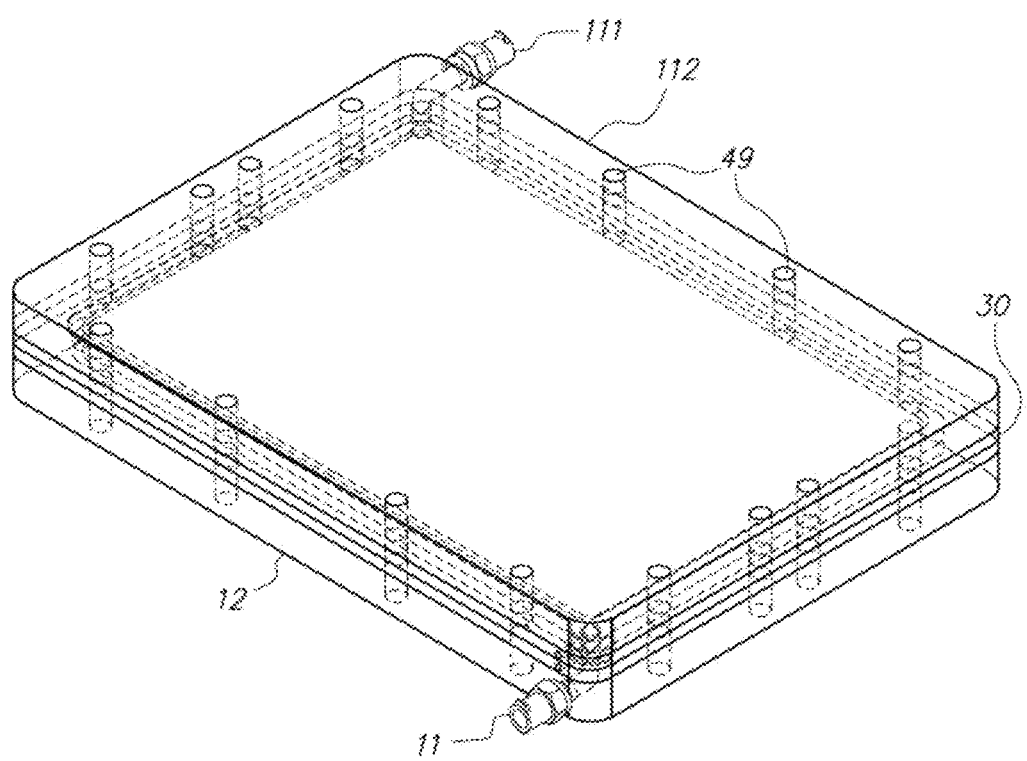
FIG. 15 is a perspective view of bioreactor case of FIG. 13.

Alternately, the feed cap 12, the intermediate module 30 and the drain cap 112 may be secured in the assembled configuration of the bioreactor case 10 of FIG. 13 by providing a feed cap 12, a drain cap 112 and an intermediate module 30 having embedded or connected magnetic members oriented for mutual attraction. FIGS. 14 and 15 illustrate an embodiment of the bioreactor case 10 having a plurality of rare earth magnets 49 embedded at a plurality of positions along the perimeter of the feed cap 12 and a corresponding plurality of rare earth magnets may be embedded in aligned positions along the perimeter of the drain cap 112.

Figure 16:
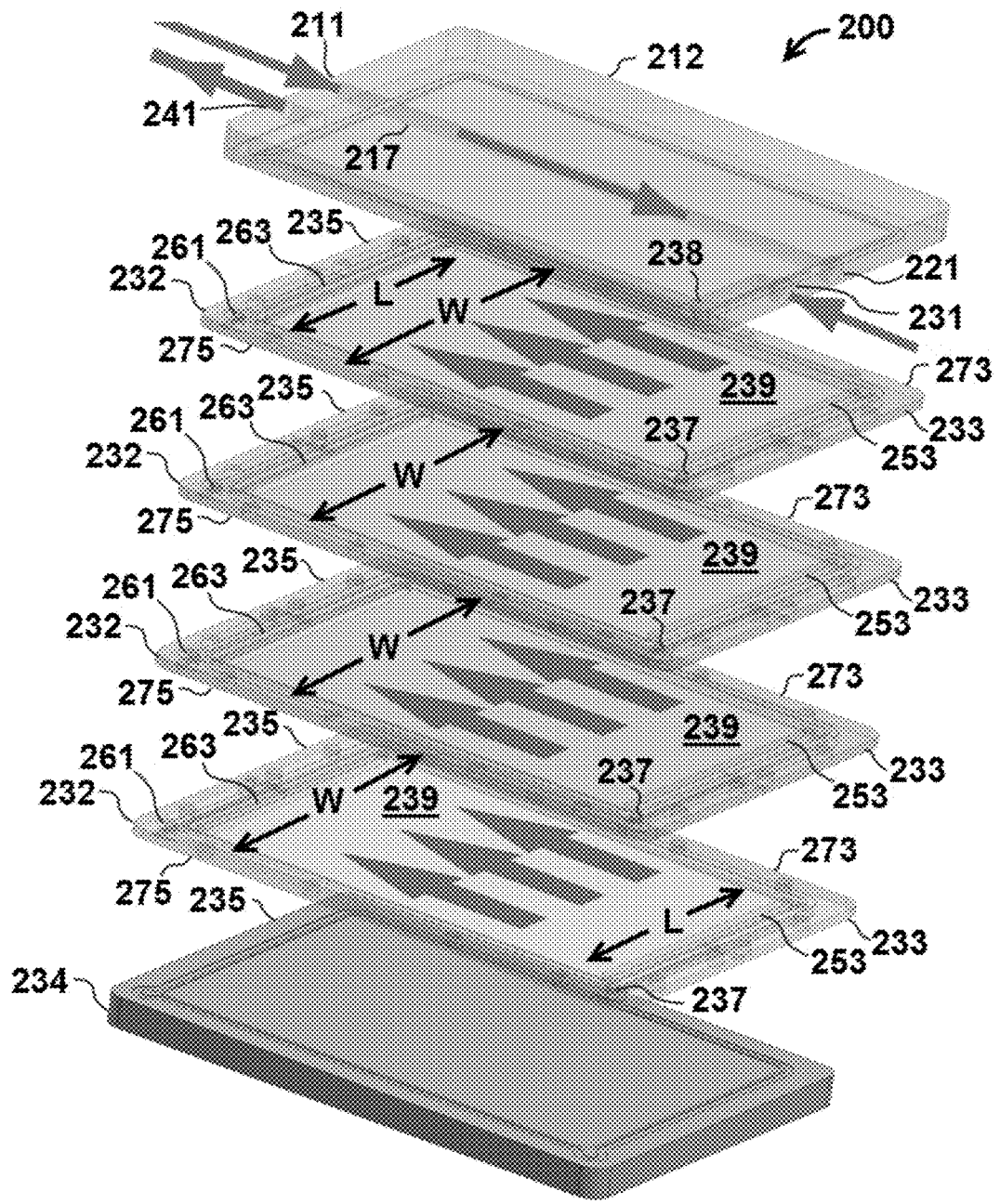
FIG. 16 is an exploded view of one embodiment of a cell preparation system according to the present disclosure.
Figure 17:
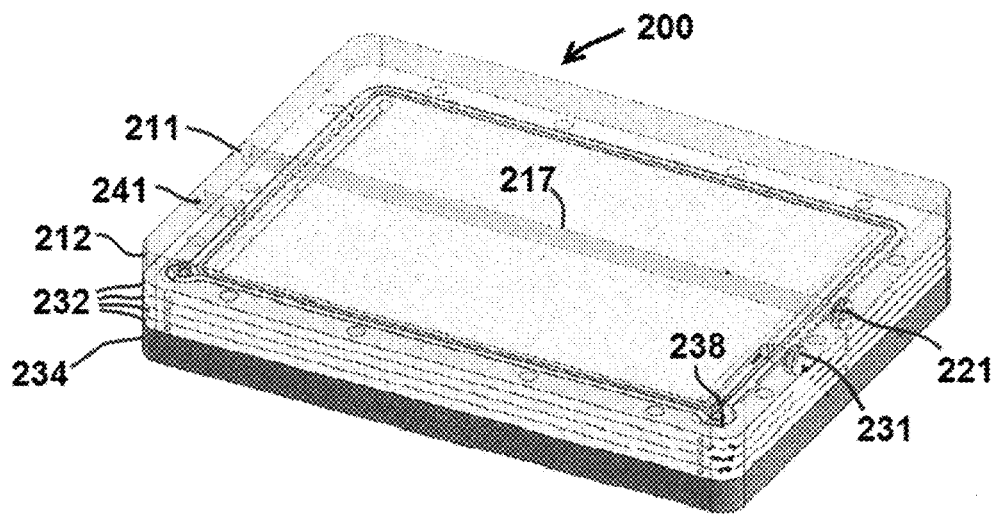
FIG. 17 is a perspective assembly view of the cell preparation system of FIG. 16.

Referring now to FIGS. 16 and 17, another embodiment of a bioreactor case 200 is shown in perspective and exploded views, respectively. For purposes of clarity, not all elements are labeled with reference numbers in each figure. Bioreactor case 200 comprises an inlet fluid feed plate 212, a plurality of intermediate module plates 232, and a base module plate 234. Each intermediate module plate 232 comprises a first end 233, a second end 235, a first side 273, and a second side 275. In addition, intermediate module plates 232 are vertically stacked between inlet fluid feed plate 212 and base module plate 234.

Figure 18:
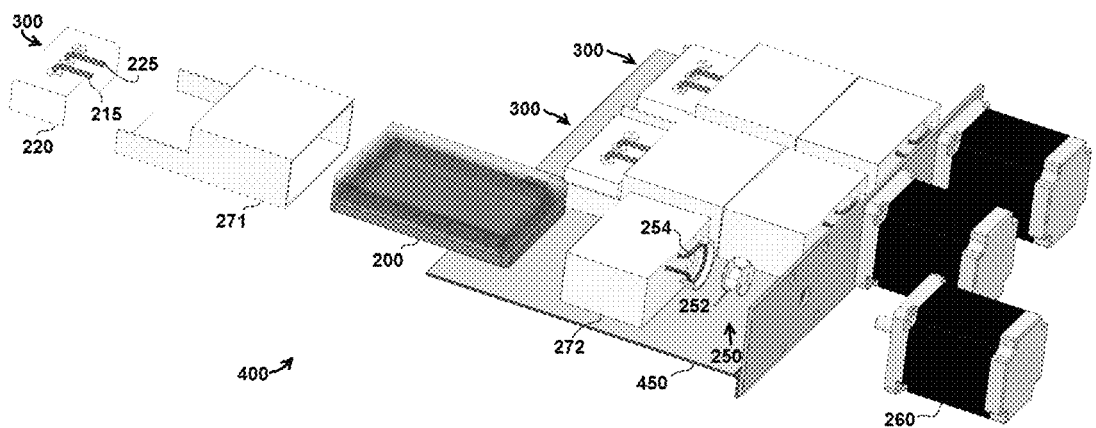
FIG. 18 is a first perspective view of a cell preparation system comprising a plurality of modular cell preparation apparatus.
Figure 19:
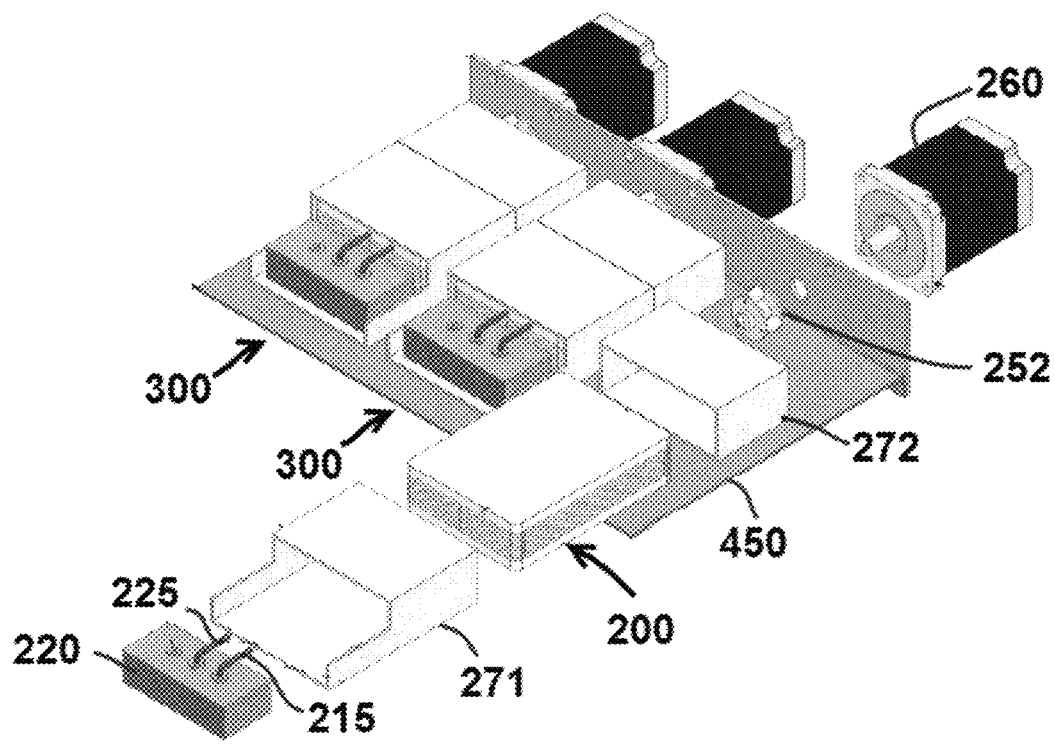
FIG. 19 is a second perspective view of the cell preparation system of FIG. 18.

As shown in FIGS. 18 and 19, bioreactor case 200 can be assembled as a component in a modular cell preparation apparatus 300. In the embodiment shown in FIGS. 18 and 19, a plurality of modular cell preparation apparatus 300 are assembled as components in a cell preparation system 400. Cell preparation system 400 comprises a base 450 configured to support multiple modular cell preparation apparatus 300. In the embodiment shown, each cell preparation system comprises bioreactor case 200, reservoir 220, first housing 271, second housing 272 and pump 250. Reservoir 220 is in fluid communication with bioreactor case 200 via supply conduit 215 and return conduit 225.

Referring specifically now to FIGS. 16 and 17, bioreactor case 200 comprises inlet fluid feed plate 212 with a central channel 217 having a first fluid inlet 211 and a first fluid outlet 221. Inlet fluid feed plate 212 also comprises a second fluid inlet 231 and a second fluid outlet 241. As shown in FIGS. 18 and 19, first fluid inlet 211 and second fluid outlet 241 may be coupled to reservoir 220, while first fluid outlet 221 and second fluid inlet 231 may be coupled to a pump 250. In certain embodiments, pump 250 may be configured as a roller (e.g. peristaltic) pump. Pump 250 comprises a rolling element 252 and a compressible conduit 254. During operation rolling element 252 is rotated by an electric motor 260. Fluid from reservoir 220 is drawn through conduit 215 into first fluid inlet 211, through central channel 217 and first fluid outlet 221 into compressible conduit 254. Fluid is then directed to second fluid inlet 231 and to a distribution port 238 in fluid communication with intermediate module plates 232.

Intermediate module plates 232 each comprise an inlet port 237 in fluid communication with distribution port 238. Each intermediate module plate 232 further comprises a distribution channel 253 in fluid communication with inlet port 237. Each distribution channel 253 and inlet port 237 are proximal to first end 233 of intermediate module plate 232. Each distribution channel 253 extends across a culture plate 239 and distributes fluid over culture plate 239. After flowing across culture plate 239, fluid is collected by gathering channel 263, which is in fluid communication with a return port 261 in each intermediate module plate 232. Gathering channel 263 and return port 261 are proximal to second end 235 of intermediate module plate 232. Accordingly, fluid must flow across culture plate 239 in order to enter gathering channel 263. Return ports 261 are further in fluid communication with second fluid outlet 241, which is in fluid communication with reservoir 220 via return conduit 225.

The flow of fluid culture plates 239 from distribution channels 253 to gathering channels 263 subjects cells on culture plates 239 to a shear stress. The ability to recycle fluid from reservoir 220 and through bioreactor case 200 (including multiple intermediate module plates 232 and culture plates 239) via pump 250 allows the shear stress to be applied for extended (theoretically unlimited) periods of time.

In exemplary embodiments, it is desirable to control the amount of shear stress applied to cells on culture plates 239 at a uniform level and to minimize the differences in applied shear stress at different locations on culture plates 239. One factor in maintaining a uniform applied shear stress to the cells is the velocity of the fluid media relative to the cells and culture plate 239. Reducing variations in the fluid velocity can help to maintain a more uniform applied shear stress. As shown in FIG. 16, distribution channels 253 and gathering channels 263 extend substantially across a width W of the surface of intermediate module plate 232 (e.g. the dimension between first side 273 and second side 275 of intermediate module plate 232). In certain embodiments, the length L of distribution channels 253 and gathering channels 263 (e.g. the distance between each end of the channels measured parallel to dimension W of intermediate module plate 232) extend across a majority of width W of intermediate module plate 232. In particular embodiments, length L is at least 70 percent, 75 percent, 80 percent, 85 percent, 90 percent, or 95 percent of width W. This configuration can provide a more uniform velocity of fluid media across culture plates 239 as compared to, for example, inlet and outlet ports that do not extend across a majority of culture plates 239. Cells adhered to culture plates 239 will in turn be subjected to a more uniform shear stress.

The level of shear stress applied to the cells can also be controlled by adjusting various operational parameters. For example, the pressure applied to the fluid via pump 250 can be altered by adjusting the amount that rolling element 252 compresses compressible conduit 254. The volume and velocity of fluid flowing across culture plates 239 can also be adjusted by varying the speed of electric motor 260, which in turn will alter the rotational speed of rolling element 252. Additional control can be accomplished by selection of specific dimensions and geometries for components including, but not limited to the surface finish (e.g. roughness), length and width of culture plates 239, as well as the distance between intermediate module plates 232.

In addition, the use of a plurality of intermediate module plates 232 with culture plates 239 in a vertical stack allows for an increased number of cells to be subjected to shear stress. Furthermore, the use of multiple modular cell preparation apparatus 300 operating in parallel in cell preparation system 400 can further increase the number of cells subjected to shear stress in preparation for further processing or analysis.

In certain embodiments, modular cell preparation apparatus 300 (operating individually or as components in cell preparation system 400) can be operated to control the hydrodynamic microenvironment to direct mechanotransduction conditioning of cells such as, but not limited to MSC, in a controlled manner. By way of example, the studies provided herein demonstrate that the methods and apparatus described condition cell populations, including for example MSC, by subjecting them to a uniform and controllable shear stress as needed to condition such cells to express a particular activity, including, but not limited to, the induction and release of immunomodulatory factors.

The studies provided in the examples below demonstrate methods that human cell cultures, for example MSC, subject to shear stress of the type similar to that provided by the present apparatus, albeit using a less flexible system, using a device that is far more limited and less preparative in the scale of its abilities to administer shear stress. However, these studies illustrate that shear stress can be used to condition cells to express a particular activity, such as, but not limited to the induction and release of immunomodulatory factors.

The results presented herein demonstrate that functional MSCs can be directly conditioned to express and produce anti-inflammatory and immunomodulatory factors. In the context of cellular therapy, this technique promises to provide relief to patients affected by or at risk for inflammation associated with injury or disease. This indicates that conditioning of MSCs using shear stress of the type provided by the present system substantially increases their ability to inhibit inflammatory cells in pre-existing inflammatory environments and may aid in the prevention and resolution of inflammation.

Moreover, by using the system described herein, conditioning can be completed more rapidly, uniformly and reliably than when using alternatively available techniques of inducing MSC cell immunomodulatory activity, including for example, the production of anti-inflammatory molecules. The system described to condition cells can be particularly advantageous when a subject's own (autologous) cells are to be used as a therapeutic and a method for cell expansion and conditioning is required.

In the absence of conditioning, naive MSCs express little to none of the key mediators of immunosuppression such as the multifunctional anti-inflammatory proteins TNF-α stimulated protein 6 (TSG-6), prostaglandin E2 (PGE2), and interleukin (IL)-1 receptor antagonist (IL1RN). As detailed in the examples below, MSCs derived from three human tissue sources, bone marrow, adipose, and amniotic fluid, were all found to be responsive to this system of shear stress-based conditioning such that activation of immunomodulatory signaling was detectable to varying extents. Specifically, evaluation of conditioned human bone marrow-derived MSCs, using laminar shear stress of the type provided by the present system stimulated profound up-regulation of gene expression with from 6- to 120-fold increases, in the transcription of MSC genes encoding TSG-6, COX-2, IL1Ra, HMOX-1, LIF, and KLF2.

Exemplary embodiments include methods for providing a population of conditioned cells, the method comprising: obtaining a population of cells and subjecting the cells to a controlled shear stress. Certain embodiments include methods for providing a population of conditioned cells, the method comprising: obtaining a population of cells; culturing said cells in a cell media; and subjecting the cells to a controllable shear stress of sufficient force to condition the cells. In some embodiments, the cells are originally obtained from a mammal. In some embodiments, the cells are originally obtained from a companion animal. In preferred embodiments, the cells are originally obtained from a human. In some embodiments, the cells are originally obtained from bone marrow. In some embodiments, the cells are originally obtained from amniotic fluid while in other embodiments. While in some embodiments, the cells are originally obtained from adipose tissue. In some embodiments, the cells subjected to a controlled shear stress are MSC.

In additional embodiments, are methods of obtaining a therapeutically effective number of conditioned cells. In some embodiments, are methods of obtaining a therapeutically effective number of cells conditioned using the apparatus and methods described herein. In some embodiments, are methods of obtaining a therapeutically effective number of cells conditioned using the method comprising: obtaining a population of cells; applying a controlled shear stress of sufficient force to condition such cells to act as desired. In some other embodiments, are methods of obtaining a therapeutically effective number of cells conditioned using the method comprising: obtaining a population of cells; applying a controlled shear stress of sufficient force to condition such cells to act as desired. In some embodiments are methods of obtaining a therapeutically effective number of cells conditioned using the method comprising: obtaining a population of cells; culturing the cells on a first culture surface in a cell media, such that the cells adhere to on the first culture surface; and applying a controlled shear stress of sufficient force to condition such cells to act as desired. In some embodiments are methods of obtaining a therapeutically effective number of cells conditioned using the method comprising: obtaining a population of cells; culturing the cells on a culture surface in a cell media, such that the cells adhere to on the barrier; and applying a controlled shear stress of sufficient force to condition such cells to act as desired.

In similar embodiments, are methods for providing a population of conditioned cells comprising: obtaining a population of cells; culturing the cells in a culture system in a cell media, such that the cells adhere to the barrier; passing the cell media over said cells to provide a controlled fluid laminar shear stress of sufficient force to condition said cells. In some embodiments, the conditioned cells express anti-inflammatory activity. In some embodiments, the anti-inflammatory activity includes increased expression of genes selected from a group comprising those that encode TSG-6, COX-2, IL1RN, HMOX-1, LIF, or KLF2. In some embodiments, the activity includes increased expression of COX2 protein by the conditioned cells.

Additional embodiments include compositions comprising cells that have been conditioned using controlled shear stress in the apparatus described in claims 1-10. Some embodiments include compositions comprising cells that have been conditioned using a method comprising: obtaining a population of cells; culturing said cells in a culture system in a cell media, such that the cells adhere to the barrier; and applying a fluid laminar shear stress of sufficient force to condition said cells. In similar embodiments, are compositions comprising cells that have been conditioned using a method for providing a population of conditioned cells comprising: obtaining a population of cells; culturing the cells in a culture system in a cell media, such that the cells adhere to the barrier; passing said cell media over said cells to provide a fluid laminar shear stress of sufficient force to condition said cells. In some embodiments, the compositions comprise conditioned cells that express anti-inflammatory activity. In some embodiments, the anti-inflammatory activity includes increased expression of genes selected from a group comprising those that encode TSG-6, COX-2, IL1RN, HMOX-1, LIF, or KLF2. In some embodiments, the compositions comprise conditioned cells that express increased levels of COX2 protein. In additional embodiments the described device and methods may be used to stimulate the expression and release of anti-inflammatory factors, which can be isolated from the media and be used as therapeutics.

In additional embodiments are methods of treating a subject in need of such a treatment with cells conditioned by the methods described. In alternative embodiments are methods of treating a subject in need of such a treatment may include factors released by cells conditioned using the described methods.

In some embodiments, methods of treating a subject include but are not limited to, obtaining a population of conditioned cells produced in accordance with the described system and administering the cells to the subject in need of treatment. In some embodiments, the subject is in need of an anti-inflammatory therapy and the population of cells are human MSC whose anti-inflammatory activity has been induced using the described system. In some embodiments, a therapeutic dose of such cells may comprise at least $1\times10^2$, $1\times10^3$, $1\times10^4$, $1\times10^5$ or $1\times10^6$ cells which are introduced into the subject in need of therapy. In some embodiments anti-inflammatory activity of the conditioned cell population can be used to treat acute disorders such as, but not limited to, muscular skeletal injuries such as orthopedic or spinal cord injury or traumatic brain injury.

Cell culture conditioning systems are described in various embodiments herein and it is appreciated that additional methods for the culture and maintenance of cells, as would be known to one of skill, may be used with the present embodiments. In certain embodiments, for culture, various matrix components may be used in culturing, maintaining, or differentiating human stem cells. In addition to those described in the examples below, for example, collagen IV, fibronectin, laminin, and vitronectin in combination may be used to coat a culturing surface as a means of providing a solid support for pluripotent cell growth. Matrigel™ may also be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

In some embodiments of cell culturing, once a culture container is full (e.g., confluent), the colony is split into aggregated cells or even single cells by any method suitable for dissociation, which cells are then placed into new culture containers for passaging. Cell passaging or splitting is a technique that enables cells to survive and grow under cultured conditions for extended periods of time. Cells typically would be passaged when they are about 70%-100% confluent.

In certain aspects, starting cells for the present conditioning system may comprise at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about $10$, $10^1$, $10^2$, $10^3$, $10^4$, $10^5$, $10^6$, $10^7$, $10^8$ cells/mL, or any range derivable therein.

As the basal medium, in addition to that described in the examples below, a range of media is available including defined medium, such as Eagle's Basal Medium (BME), BGJb, CMRL 1066, Glasgow MEM, Improved MEM Zinc Option, Iscove's modified Dulbecco's medium (IMDM), Medium 199, Eagle MEM, αMEM, DMEM, Ham, RPMI 1640, and Fischer's media. Additional examples of media that may be used according to the embodiments include, without limitation, Lonza Therapeak (chemically defined) medium, Irvine Scientific Prime-XV (SFM or XSFM), PromoCell MSC Growth Medium (DXF), StemCell Technologies Mesencult (ACF), or human platelet or platelet-lysate enriched medium.

In further embodiments, the media can also contain supplements such as B-27 supplement, an insulin, transferrin, and selenium (ITS) supplement, L-Glutamine, NEAA (non-essential amino acids), P/S (penicillin/streptomycin), N2 supplement (5 μg/mL insulin, 100 μg/mL transferrin, 20 nM progesterone, 30 nM selenium, 100 μM putrescine and β-mercaptoethanol (β-ME). It is contemplated that additional factors may or may not be added, including, but not limited to fibronectin, laminin, heparin, heparin sulfate, retinoic acid.

Additional factors may be added to a media for use in conjunction with sheer stress for generating a conditioned composition, such as a population of conditioned cells. Thus, in some embodiments, at least one chemical modulator of hematopoiesis may be applied before, during, or after biomechanical stimulation. Examples of additional components that could be added to media include, without limitation, Atenolol, Digoxin, Doxazosin, Doxycycline, Fendiline, Hydralazine, 13-hydroxyoctadecadienoic acid (13(s)-HODE), Lanatoside C, NG-monomethyl-L-arginine (L-NMMA), Metoprolol, Nerifolin, Nicardipine, Nifedipine, Nitric oxide (NO) or NO signaling pathway agonists, 1H-[1,2,4]oxadiazolo-[4,3-a]quinoxalin-1-one (ODQ), Peruvoside, Pindolol, Pronethalol, Synaptosomal protein (SNAP), Sodium Nitroprusside, Strophanthidin, Todralazine, 1,5-Pentamethylenetetrazole, Prostaglandin E 2 (PGE2), PGE2 methyl ester, PGE2 serinol amide, 11-deoxy-16,16-dimethyl PGE2, 15(R)-15-methyl PGE2, 15 (S)-15-methyl PGE2, 6,16-dimethyl PGE2, 16,16-dimethyl PGE2 p-(p-acetamidobenzamido) phenyl ester, 16-phenyl tetranor PGE2, 19(R)-hydroxy PGE2, Prostaglandin B2, Prostacyclin (PGI2, epoprostenol), 4-Aminopyridine, 8-bromo-cAMP, 9-deoxy-9-methylene PGE2, 9-deoxy-9-methylene-16,16-dimethyl PGE2, a PGE2 receptor agonist, Bapta-AM, Benfotiamine, Bicuclline, (2'Z,3'E)-6-Bromoindirubin-3'-oxime (BIO), Bradykinin, Butaprost, CaylO397, Chlorotrianisene, Chlorpropamide, Diazoxide, Eicosatrienoic Acid, Epoxyeicosatrienoic Acid, Flurandrenolide, Forskolin, Gaboxadol, Gallamine, Indanyloxyacetic acid 94 (IAA 94), Imipramine, Kynurenic Acid, L-Arginine, Linoleic Acid, LY171883, Mead Acid, Mebeverine, 12 Methoxydodecenoic acid, N-Formyl-Met-Leu-Phe, Prostaglandin E2 receptor EP2-selective agonist (ONO-AEl-259), Peruvoside, Pimozide, Pindolol, Sodium Nitroprusside, Sodium Vanadate, Strophanthidin, Sulprostone, Thiabendazole, Vesamicol, 1,2-Didecanoyl-glycerol (10:0), 11,12 Epoxyeicosatrienoic acid,l-Hexadecyl-2-arachidonoyl-glycerol, 5-Hydroxydecanoate, 6-Formylindolo [3,2-B] carbazole, Anandamide (20:3, n-6), Carbacyclin, Carbamyl-Platelet-activating factor (C-PAF), or S-Farnesyl-L-cysteine methyl ester.

In further aspects, a media can include one or more growth factors, such as members of the epidermal growth factor family, e.g., EGF, members of the fibroblast growth factor family (FGFs) including FGF2 and/or FGF8, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin amnionless, TGF, BMP, and GDF antagonists could also be added in the form of TGF, BMP, and GDF receptor-Fc chimeras. Other factors that may or may not be added include molecules that can activate or inactivate signaling through Notch receptor family, including but not limited to proteins of the Delta-like and Jagged families as well as gamma secretase inhibitors and other inhibitors of Notch processing or cleavage such as DAPT. Additional growth factors may include members of the insulin like growth factor family (IGF), the wingless related (WNT) factor family, and the hedgehog factor family.

In still further aspects, a media can include one or more priming agents such as an inflammatory cytokine, LPS, PHA, Poly I:C, and/or ConA. Additional priming agents that may be used according the embodiments include those detailed Wagner et al., 2009, which is incorporated herein by reference. Additional factors may be added particularly in further differentiation medium to promote cell progenitor proliferation and survival as well as self renewal and differentiation, including but not limited to dimethyl-prostaglandin E2, iloprost, and other similar products of arachidonic acid metabolism.

The medium can be a serum-containing or serum-free medium. The serum-free medium may refer to a medium with no unprocessed or unpurified serum and accordingly, can include media with purified blood-derived components or animal tissue-derived components (such as growth factors). From the aspect of preventing contamination with heterogeneous animal-derived components, serum can be derived from the same animal as that of the cell(s).

The medium may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. WO98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5, or 0.01, 0.02, 0.03, 0.04, 0.05, 0.1, 0.2, 0.5, 0.8, 1, 1.5, 2, 2.5, 5, 7.5, 10 mM or any intermediate values, but the concentration is particularly not limited thereto as long as it is appropriate for culturing the stem cell(s).

The cells may be cultured in a volume of at least or about 0.005, 0.010, 0.015, 0.2, 0.5, 1, 2, 5, 10, 20, 30, 40, 50, 100, 150, 200, 250, 300, 350, 400, 450, 500, 550, 600, 800, 1000, 1500 mL, or any range derivable therein, depending on the needs of the culture. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture surface and chamber formed between the wall 13 of the feed cap 12 and the barrier 39 of the intermediate module 30 when the apparatus is assembled can be prepared with cellular adhesive or not depending upon the purpose. The cellular adhesive culture vessel can be coated with a suitable substrate for cell adhesion (e.g. extracellular matrix [ECM]) to improve the adhesiveness of the vessel surface to the cells. The substrate used for cell adhesion can be any material intended to attach stem cells or feeder cells (if used). Non-limiting substrates for cell adhesion include collagen, gelatin, poly-L-lysine, poly-D-lysine, poly-D-ornithine, laminin, vitronectin, and fibronectin and mixtures thereof, for example, protein mixtures from Engelbreth-Holm-Swarm mouse sarcoma cells (such as Matrigel™ or Geltrex) and lysed cell membrane preparations. In specific embodiments culture includes a matrix comprising poly-L-lysine (or poly-D-lysine) and laminin.

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 7%, or any range derivable therein. The oxygen tension can be at least or about 1, 5, 8, 10, 20%, or any range derivable therein.

Essentially free of an "externally added" component refers to a medium that does not have, or that have essentially none of, the specified component from a source other than the cells in the medium. "Essentially free" of externally added growth factors or polypeptides, such as FGF or EGF etc., may mean a minimal amount or an undetectable amount of the externally added component. For example, a medium or environment essentially free of FGF or EGF polypeptide can contain less than 1, 0.9, 0.8, 0.7, 0.6, 0.5, 0.4, 0.3, 0.2, 0.1, 0.01, 0.001 ng/mL or any range derivable therein.

In some embodiments, cells conditioned using the system described have a variety of therapeutic uses. In particular, if the cells are human MSCs, diseases or disorders for which such conditioned cells can be used therapeutically, or alternatively those diseases or disorders for which therapy with the factors produced and isolated from cultured cells, including but not limited to MSCs subjected to conditioning with the system described include, but are not limited to, autoimmune disorders (including but not limited to Rheumatoid Arthritis (RA), Systemic Lupus Erythematosis (SLE)), graft-versus-host disease, Crohn's disease, inflammatory bowel disease, neurodegenerative disorders, neuronal dysfunctions, disorders of the brain, disorders of the central nervous system, disorders of the peripheral nervous system, neurological conditions, disorders of memory and learning, cardiac arrhythmias, Parkinson's disease, ocular disorders, spinal cord injury, disorders requiring neural healing and regeneration, Multiple Sclerosis (MS), Amyelotrophic Lateral Sclerosis (ALS), Parkinson's disease, stroke, chronic or acute injury, bone repair, traumatic brain injury, orthopedic and spinal conditions, cartilage skeletal or muscular disorders, osteoarthritis, osteonecrosis, cardiovascular diseases, blood vessel damage linked to heart attacks or diseases such as critical limb ischemia, peripheral artery disease, atherosclerosis, and those benefiting from neovascularization, wounds, burns and ulcers.

In certain embodiments the presently disclosed system can be applied to condition cells and improve their immune regulatory properties. In certain embodiments, such compositions can be administered in combination with one or more additional compounds or agents ("additional active agents") for the treatment, management, and/or prevention of among other things autoimmune diseases and disorders. Such therapies can be administered to a patient at therapeutically effective doses to treat or ameliorate, among other things, immunoregulatory disease or disorders.

Toxicity and therapeutic efficacy of such conditioned cell or factor compositions can be determined by standard pharmaceutical procedures, using for example, cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, expressed as the ratio $LD_{50}/ED_{50}$. Compositions that exhibit large therapeutic indices are preferred. Compounds that exhibit toxic side effects may be used in certain embodiments, however, care should usually be taken to design delivery systems that target such compositions preferentially to the site of affected tissue, in order to minimize potential damage to unaffected cells and, thereby, reduce side effects.

Data obtained from cell culture assays and animal studies can be used in formulating a range of dosages for use in humans. The dosages of such compositions lie preferably within a range of circulating concentrations that include the $ED_{50}$ with little or no toxicity. The dosage may vary within this range depending on the dosage form employed and the route of administration utilized. For any composition, the therapeutically effective dose may be estimated initially from cell culture assays. A dose may be formulated in animal models to achieve a circulating plasma concentration range that includes the $IC_{50}$ (i.e., the concentration of the test composition that achieves a half-maximal inhibition of symptoms) as determined in cell culture. Such information can be used to more accurately determine useful doses in humans. Plasma levels may be measured, for example, by high performance liquid chromatography.

When the therapeutic treatment of among other things autoimmune disorders is contemplated, the appropriate dosage may also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies will help establish safe doses.

Additionally, the bioactive agent may be coupled or complexed with a variety of well-established compositions or structures that, for instance, enhance the stability of the bioactive agent, or otherwise enhance its pharmacological properties (e.g., increase in vivo half-life, reduce toxicity, etc.).

Cells conditioned using the present system or factors released from such cells and other such therapeutic agents can be administered by any number of methods known to those of ordinary skill in the art including, but not limited to, cell insertion during surgery, intravenous (I.V.), intraperitoneal (I.P.), intramuscular (I.M.), or intrathecal injection, inhalation, subcutaneous (sub-q), or topically applied (transderm, ointments, creams, salves, eye drops, and the like).

The following examples section provides further details regarding examples of various embodiments. It should be appreciated by those of skill in the art that the techniques disclosed in the examples that follow represent techniques and/or compositions discovered by the inventors to function well. However, those of skill in the art should, in light of the present disclosure, appreciate that many changes can be made in the specific embodiments which are disclosed and still obtain a like or similar result without departing from the spirit and scope of the invention. These examples are illustrations of the methods and systems described herein and are not intended to limit the scope of the invention. Non-limiting examples of such include, but are not limited to, those presented below.

As used herein, and unless otherwise indicated, the terms "treat," "treating," "treatment" and "therapy" contemplate an action that occurs while a patient is suffering from a disease or disorder that reduces the severity of one or more symptoms or effects of such disease or disorder. Where the context allows, the terms "treat," "treating," and "treatment" also refers to actions taken toward ensuring that individuals at increased risk of a disease or disorder, are able to receive appropriate surgical and/or other medical intervention prior to onset of a disease or disorder. As used herein, and unless otherwise indicated, the terms "prevent," "preventing," and "prevention" contemplate an action that occurs before a patient begins to suffer from a disease or disorder, that delays the onset of, and/or inhibits or reduces the severity of a disease or disorder.

As used herein, and unless otherwise indicated, the terms "manage," "managing," and "management" encompass preventing, delaying, or reducing the severity of a recurrence of a disease or disorder in a patient who has already suffered from such a disease, disorder or condition. The terms encompass modulating the threshold, development, and/or duration of a disease or disorder or changing how a patient responds to a disease or disorder.

As used herein, and unless otherwise specified, a "therapeutically effective amount" of cells, factor or compound is an amount sufficient to provide any therapeutic benefit in the treatment or management of a disease or disorder, or to delay or minimize one or more symptoms associated with a disease or disorder. A therapeutically effective amount means an amount of the cells, factor or compound, alone or in combination with one or more other therapies and/or therapeutic agents that provide any therapeutic benefit in the treatment or management of a disease or disorder. The term "therapeutically effective amount" can encompass an amount that alleviates a disease or disorder, improves or reduces a disease or disorder, improves overall therapy, or enhances the therapeutic efficacy of another therapeutic agent.

As used herein, and unless otherwise specified, a "prophylactically effective amount" of cells, factor or compound is an amount sufficient to prevent or delay the onset of a disease or disorder, or one or more symptoms associated with a disease or disorder, or prevents or delays its recurrence. A prophylactically effective amount of cells, factors or compound means an amount of the cells, factor or compound, alone or in combination with one or more other treatment and/or prophylactic agent that provides a prophylactic benefit in the prevention of a disease or disorder. The term "prophylactically effective amount" can encompass an amount of cells, factor or compound that prevents a disease or disorder, improves overall prophylaxis, or enhances the prophylactic efficacy of another prophylactic agent. The "prophylactically effective amount" can be prescribed prior to, for example, the disease or disorder.

As used herein, "patient" or "subject" includes mammalian organisms which are capable of suffering from a disease or disorder as described herein, such as human and non-human mammals, for example, but not limited to, rodents, mice, rats, non-human primates, companion animals such as dogs and cats as well as livestock, e.g., sheep, cow, horse, etc.

As used herein, "MSC" are Mesenchymal Stem Cells, such cells have also been referred to as Mesenchymal Stromal Cells.

As used herein, "controlled shear stress" refers to the ability to set the amount of shear stress applied to the cells by adjusting the flow rate of media across the surface. The stress is uniformly applied across the entire surface area of the plate.

As used herein, "conditioned cells" refers to cells which express additional functionality as a result of having been exposed to a shear stress.

The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Without further elaboration, it is believed that one skilled in the art can, using the description herein, utilize the present methods to its fullest extent. The embodiments described herein are to be construed as illustrative and not as constraining the remainder of the disclosure in any way whatsoever. While preferred embodiments have been shown and described, many variations and modifications thereof can be made by one skilled in the art without departing from the spirit and teachings of the presently disclosed methods.

Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they are consistent with the present disclosure set forth herein.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A pilot study was conducted to provide proof of principle that fluid shear stress can be used to condition stem cells, alter gene expression, and enhance functional activities. To exemplify the conditioning activity of shear stress of the type provided by the present system, but on a much smaller analytical scale, force (shear stress) was applied using custom fabricated slides or IBIDI® small-scale microfluidics channel slides obtained from IBIDI, LLC. (Verona, Wis., USA). Human samples were harvested from bone marrow (BM), amniotic fluid (AF), or adipose (AD) tissue, processed for isolation and expansion of hMSC, and stored frozen. Frozen hMSCs were thawed and seeded into T225 cell culture flasks with 50 ml Minimum Essential Medium (MEM-α) (20% FBS, 5% Penicillin/Streptomycin, 5% Glutamine). The media was replaced every 3-4 days. hMSCs were maintained in culture until they were almost 100% confluent. The cells had a fibroblastic phenotype. Prior to seeding the cells onto the device (IBIDI® microfluidic channel slide or a custom fabricated slide) to provide fluid laminar shear stress similar to, but on a far more limed scale than that which is provided by the instant system, the culture surfaces were pre-coated with 100 ug/ml fibronectin in PBS for 30-45 min at 37° C. and washed 2× with PBS before seeding cells and allowed to sit in the incubator for 30-45 minutes while cells were prepared for seeding. Cultured hMSC were prepared by removing the media from the T225 flask using a vacuum and glass Pasteur pipette, the cells were washed 1× with room temperature PBS, which was removed by aspiration. 3 ml of a 0.25% trypsin solution was added and the flask was incubated at 37° C. for 5 min. Following this incubation, the flask was removed from the incubator and tapped vigorously to dislodge the cells. The flask was examined under a dissecting microscope to ensure that all of the cells had detached and were free-floating. At this point 9 ml of MEM-α was added to the flask and the total volume (12 ml) was removed and placed in a 15 ml conical tube. The tube was placed in a centrifuge and spun at 300 RCF for 5 minutes at room temperature. The supernatant was aspirated, leaving a small amount of media above the cell pellet, 3 ml MEM-α was added and the cell pellet was resuspended in this media. The number of live cells present was determined using trypan blue dye exclusion. Live cell counts were determined on a hemacytometer and the cells were resuspended to obtain the desired concentration for each assay (see Table 1). IBIDI channels were utilized to provide fluid laminar shear stress similar to, but less well controlled than, the type provided by the instant system. Cells were allowed to sit for 30-45 minutes before filling wells with 60 ul media per well (if too much time passes, the media will begin to evaporate from the channels). Cells were allowed to incubate for 12-18 hours. Tubing was then attached to the IBIDI® slide in the safety cabinet with a clean three way stopcock (all previously autoclaved or EtO sterilized, the three stop tubing required for use with a peristaltic pump may be EtO or UV sterilized) and then transferred to incubator. IBIDI channel experiments recirculated a total volume of 6 ml and large fabricated slide experiments recirculated 50 ml total volume. A peristaltic or Harvard syringe pump was programmed to push media across the culture surface at 15 dyne/cm2. Fluid shear stress was applied for 3, 6 or 8 hours.

TABLE 1

| Assay | Cell Concentration (cells/ml) | Culture Platform | Total Volume in channel | Time of Shear Exposure |
|---|---|---|---|---|
| qRT PCR | $3 \times 10^6$ | IBIDI | 30 ul | 3, 6, 8 hours |
| Western Blot | $3 \times 10^6$ | IBIDI | 30 ul | 8 hours |
| NF-kB Binding Assay | $2 \times 10^6$ | Custom | 10 ml | 8 hours |
| In Vivo Rat Experiments | $2 \times 10^6$ | Custom | 10 ml | 8 hours |
| ELISA assay | $2 \times 10^5$ | IBIDI | 30 ul | 3, 8 hours |
| IF Staining | $2 \times 10^5$ | IBIDI | 30 ul | 3 hours |

Immunomodulatory Changes Due to Fluid Laminar Shear Stress

Figure 20:
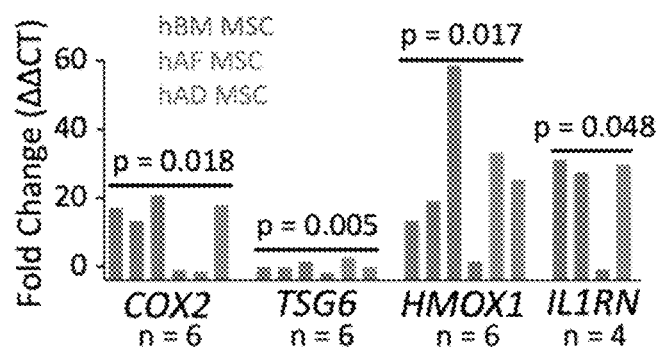
FIG. 20 graphs demonstrate that transcriptional induction is robust for COX2, TSG6, HMOX1, and IL1RN in fluid shear stressed human MSCs. hBM MSC, human bone marrow MSC (first four bars in each graph); hAF MSC, amniotic fluid MSC (second to last bar in each graph); hAD MSC, adipose-derived MSC (last bar in each graph). P-values calculated by paired t-test, equal variance.

Naive MSCs do not express key mediators of immunosuppression, such as the multifunctional anti-inflammatory proteins such as TNF-α stimulated protein 6 (TSG-6), prostaglandin E2 (PGE2), and interleukin (IL)-1 receptor antagonist (IL1RN). MSCs derived from three human tissue sources, bone marrow, adipose, and amniotic fluid, were all found to be responsive to shear stress to varying extents. For example, a shear stress applied at a force of 15 dyne/cm$^2$ activated immunomodulatory signaling in MSCs collected from multiple human tissues. Evaluation of bone marrow-derived MSCs, laminar shear stress stimulated profound up-regulation, from 6- to 120-fold increases, in transcription of MSC genes encoding TSG-6, COX-2, IL1RN, HMOX-1, LIF, and KLF2. See for example (FIG. 20).

Figure 21:
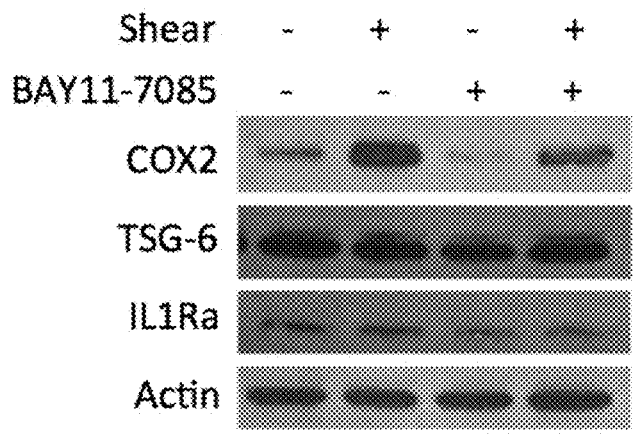
FIG. 21 illustrates representative Western blots showing increased intracellular COX2 protein, which is reduced by NF-kB antagonist BAY11-7085 (10 µM).
Figure 22:
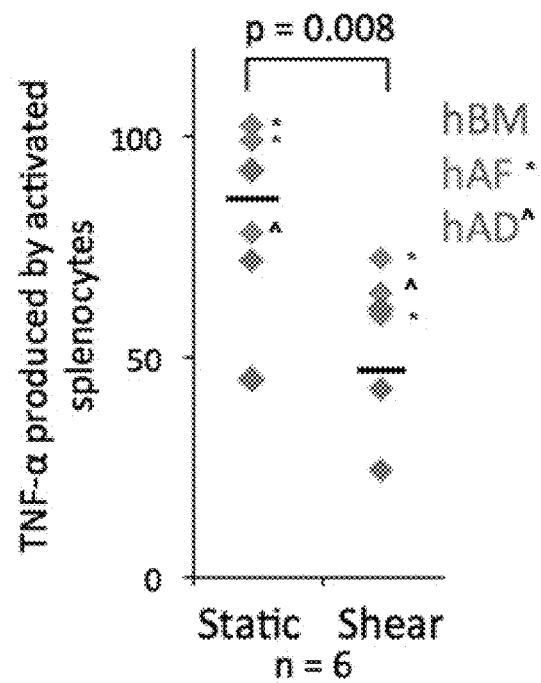
FIG. 22 illustrates TNF-α cytokine suppression assays that highlight functional enhancement of MSC immunomodulation. Human MSCs preconditioned by mechanical force (15 dyne/cm2 shear stress for 3 hrs) are placed in static co-culture with lipopoly-saccharide (LPS) or phytohaemagglutinin (PHA)-activated splenocytes including macrophages, neutrophils, NK, B, and T cells. Results of the assays show that TNF-α secretion by splenocytes is reduced by 10-50% when MSCs are transiently conditioned with shear stress. Lower values correspond to greater anti-inflammatory potency. hBM MSC, human bone marrow MSC; hAF MSC, amniotic fluid MSC (indicated by a "*" in graph); hAD MSC, adipose-derived MSC (indicated by a "^" in graph). P-values calculated by paired t-test, equal variance.
Figure 23:
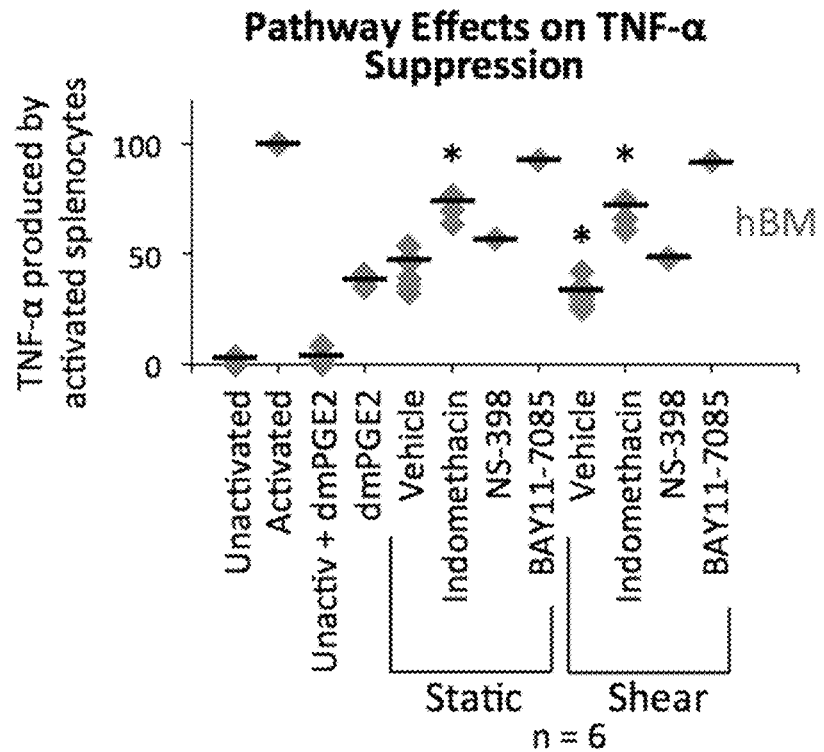
FIG. 23 illustrates inhibition of COX2 (Indomethacin, 10 µM; NS-398, 10 µM) and NF-kB (BAY11-7085, 10 µM) abrogate the positive effects of shear stress, whereas ectopic dmPGE2 (10 µM) mimics MSC suppression. Asterisks indicate p<0.001 compared to Static Vehicle. n=6 indicates six different MSC donor lines included in data shown.
Figure 24:
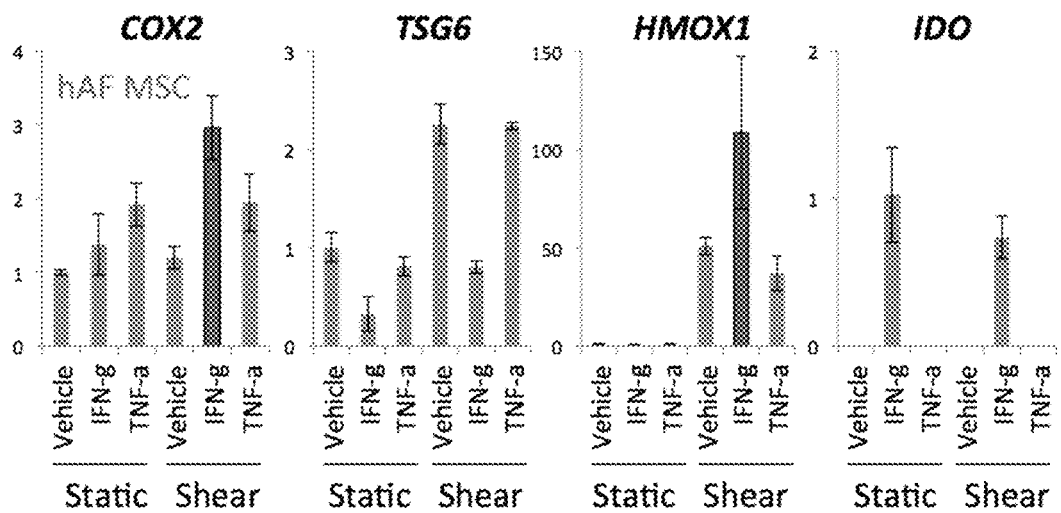
FIG. 24 illustrates that priming agents complement shear-induced anti-inflammatory signaling. Darkened bars represent treatment combinations that indicate a substantial induction of the pathway by shear stress and cytokines (IFN-γ, 20 ng/ml; TNF-α, 50 ng/ml). In this low-performance human amniotic MSC line, TSG6 was induced by shear stress only. IDO was induced by IFN-γ only. hAF MSC, human amniotic fluid MSC.

Similarly it was determined utilizing commercially available ELISAs that the media from human MSCs cultures that had been subject to fluid shear stress also contained immunomodulatory proteins, such as prostaglandin E2. In addition, Western blotting confirmed elevated protein levels (translation) of COX2, TSG6, and IL1RN. Actin protein expression levels, which are constant, were used as a control for baseline protein expression. In this study, it was determined that after exposure of human MSC (derived from hBM, human bone marrow MSC; hAF MSC, amniotic fluid MSC; hAD MSC, adipose-derived MSC) to 8 hours of fluid shear stress, there was a significant increase in the expression of COX2 protein as compared with media obtained from MSC that were not subject to fluid shear stress. It was also determined that this induction could be abrogated by the addition of 10 uM of the NF-kappaB antagonist BAY11-7085 (FIG. 21). Furthermore by utilizing commercially available ELISAs, it was determined that the media from human MSCs cultures that had been subject to fluid shear stress for as little as 3 hours had immunosuppressive activity, as evidenced by the 10-50% reduction in TNF-α when treated hMSCs were co-cultured with activated immune cells from the spleen (FIG. 22). It was also determined using cytokine suppression assays that application of COX or NF-kB inhibitors abrogated the ability of shear treated MSC to suppress TNF-α production; whereas, addition of a stabilized synthetic form of PGE2 (dmPGE2) reduced TNF-α to levels produced in the presence of sheared MSCs (FIG. 23). Additional evidence further suggests that sheared MSCs may be more responsive to other priming agents than MSC that have not been subject to a fluid shear stress, as a greater induction of COX2 and HMOX1 occurred with the addition of IFN-γ (FIG. 24). Thus, indicating that human MSC subject to fluid shear stress may act synergistically with cytokines when presented in, for example, combination therapies.

It was further determined that naive MSCs exposed to shear stress, with no preconditioning by inflammatory cytokines, were capable of blocking TNF-α secretion by lipopolysaccharide (LPS)-activated mouse splenocytes (ranging from complete inhibition to 2-fold reduction below MSC cultured under static conditions, depending upon MSC donor and source variability).

Neuroprotective Abilities:

Studies were performed to establish that cells such as MSC exposed to controlled shear stress can provide neuroprotection following, for example, traumatic brain injury (TBI). To do this a rat model was utilized to evaluate functional outcomes. Controlled cortical impact (CCI) in the rat presents morphologic and cerebrovascular injury responses that resemble human head trauma. Thus, characterization of the cellular and molecular alterations that potentiate neurological damage and inflammation provides a powerful tool to measure potential clinical efficacy of MSC preconditioning.

Twelve (12) rats were predicted to be necessary per condition to achieve 80% power, at an alpha error level of 0.05 (SAS predictive analytics software). Cells to be administered for cellular therapy were bone marrow-derived MSCs. MSCs were exposed to static conditions or to shear stress for 3 hrs at an intensity of 15 dyne/cm2, a fluid flow rate and duration demonstrated to produce robust induction of COX2, TSG6, IL1RN, and HMOX1 and to suppress cytokine production in activated immune cells. Immediately following application of force by the large capacity lateral flow system, 10×10$^6$ cells/kg MSCs were transferred to recipient rats via tail vein injection (approximate dose of 2.5×10$^6$ MSCs per rat).

Blood-brain barrier (BBB) permeability was determined using standard methods for examining leakage across the vasculature (utilizing dextran beads in suspension as described herein). Injury at the right parietal association cortex was introduced in male rats (225-250 grams) by a CCI device (Leica Impactor 1). In parallel, control rats were treated with CCI alone or simply anesthetized (sham control). Forty eight (48) hours after injury, the MSCs were administered. Twenty-four (24) hrs after the injection of MSCs, fluorescently conjugated Alexa 680-dextran beads (10 kDa, 0.5 ml of 1 mg/ml) were delivered via tail vein. Thirty (30) minutes after this dye was injected, animals were euthanized and perfused with 4% paraformaldehyde. Fixed brains were sectioned coronally at 1 mm thickness. Vascular leakage was measured by fluorescence intensity of brain sections in a LI-COR Odyssey CLx infrared laser scanner using 700 and 800 nm channels (800 nm signal was used for background subtraction). Histological analysis of the frequencies of certain immune and neural cell types that are known to be rapidly altered in response to neuroinflammation and are important indicators of prognosis. In future studies, in an independent cohort of rats, brain sections of between 8 to 50 um will be analyzed for inflammatory phenotypes in the CNS by immunohistochemistry using antibodies to detect microglia (Iba1, ED1 or CD63), infiltrating neutrophils (RP-3), astroglia (GFAP), and neurons (NeuN), as well as an indicator of cell death (cleaved caspase 3). Staining of brain sections will be done using a standard free floating staining protocol or slide-mounted cryosections.

Cognitive recovery of treated and control rats can be assessed by a classic hippocampus-dependent spatial learning task, the Morris water maze, in which rats locate an underwater platform on the basis of extra-maze cues. For these studies, two (2) weeks following injury, learning is measured by speed, time spent in each quadrant, and distance of the path taken to find the platform. The same individuals will be tested at 4 weeks post injury for memory function by the same measures in the maze. The anticipated results are that delivery of sheared MSCs will reduce BBB permeability and inflammatory cell phenotypes in the brain relative to naïve static-cultured MSC and will also result in improved cognitive recovery.

Example 2

Injury Alters the Frequency of MSCs in the Bone Marrow

Chronic inflammation in traumatic brain injury is perpetuated by monocytes and lymphocytes of the innate and adaptive immune systems. MSCs are reported to home from the bone marrow to sites of injury and inflammation, yet detailed analysis of MSC trafficking from the marrow in this context is lacking. To monitor changes in MSC frequency caused by injury, a rat model of traumatic brain injury was established which presents morphologic and cerebrovascular injury responses that resemble human head trauma. Briefly, controlled cortical impact (CCI) was delivered to the exposed right parietal association cortex adjacent to the midline suture. In parallel, sham controls were anesthesized and incisions were made without injury. The frequency of CD105+ MSCs were examined within the bone marrow and it was found that the absolute number of CD105+ MSCs was significantly decreased 24 hours after injury (FIGS. 25A and 25B). These data suggest that MSCs respond to injury by egress from the bone marrow, much as might be observed by hematopoietic stem or progenitor cells, thus increasing the likelihood that MSCs are exposed directly to hemodynamic forces present within the blood stream and on the vascular wall. Importantly, intravenous administration of human MSCs preconditioned by 3 hours of 15 dyne/cm$^2$ WSS significantly elevated CD105+ MSC frequency in the bone marrow of injured rats when administered 24 hours after CCI (FIGS. 25C and 25D). At 72 hours post-CCI, CD105+ cell frequency was significantly higher when either static cultured or WSS-exposed MSCs were administered, and the protective effect on the bone marrow was significantly greater when MSCs were preconditioned by WSS.

Materials and Methods

Cell Culture—Bone marrow MSCs were derived from whole bone marrow from independent human donors (AllCells). Briefly, mononuclear cells were enriched in the buffy layer of whole bone marrow by phase separation in FicollPaque. Cells were either cryopreserved or resuspended for immediate expansion in complete culture medium consisting of MEM-α (Thermo Scientific), 20% fetal bovine serum (Atlanta Biologicals), 100 units/ml penicillin (Gibco), 100 pg/ml streptomycin (Gibco), and 2 mM L-glutamine (Gibco). Nonadherent cells were removed after 2 days. Adherent colonies were expanded further and frozen as Passage 1. Thawed MSCs were plated at $1\times10^5$ cells/ml, and medium was changed every three days. At 80% confluence, cells were passaged into IBIDI channels (μ-Slide VI 0.4) at a density of $3\times10^6$ cells/ml for qRT PCR, immunoblotting, and rat CCI experiments and at $5\times10^5$ cells/ml for ELISA and immunofluorescence experiments. Following attachment to the culture surface, syringe pumps (PhD ULTRA programmable, Harvard Apparatus) or peristaltic pumps (REGLO analog MS4/12, Ismatec) were used to produce laminar shear stress of 15 dyne/cm$^2$.

Controlled cortical impact (CCI)—A CCI device (Leica IMPACT ONE™) was used to deliver a single impact of 3.1 mm compression at 6 m/sec at the right parietal association cortex (adjacent to midline suture between bregma & lambda) using a 6 mm impactor tip on exposed brain in male rats (225-250 grams). In parallel, control rats were treated with CCI alone or simply anesthesized (sham control). In cell therapy experiments, low passage (P2-5) MSCs were cultured under static conditions or shear stress of 15 dyne/cm$^2$ for 3 hrs. Recipient rats received MSCs ($10\times10^6$ cells/kg) via tail vein within 2 hrs of shear exposure. At time of sacrifice, rats were perfused with 4% paraformaldehyde and tissues were further fixed after collection. All experiments were conducted in compliance with guidelines from the University of Texas Health Science Center Institutional Animal Care and Use Committee.

Histological processing of rat tissues—Rat tibias were harvested and the muscle surrounding the bone was carefully removed. The bones were further fixed in 4% paraformaldehyde and decalcified using 10% EDTA. Once decalcified, the bones were transferred to the Histology Core at UT Medical School for grossing, paraffin embedding, and sectioning.

Immunostaining of bone barrow—Paraffin embedded sections were baked at 60° C. for 20 mins and serially rehydrated in xylene and varying grades of ethanol. Heat-induced epitope retrieval was performed using DAKO Target Antigen Retrieval Solution (pH 6.1). Endogenous peroxidase was blocked with 0.3% $H_2O_2$. Slides were blocked with 2.5% BSA for 1 hr and incubated overnight with anti-CD105 antibody (1:200, SN6, Ab11414) in 2.5% BSA. Immunoperoxidase detection was performed using the Vector ABC kit and DAKO DAB kit (VECTASTAIN® Elite ABC kit; PK-6102, Dako DAB kit; K3468) according to manufacturer instructions and counterstained with Nuclear Fast Red or CAT Hemotoxylin (Vector Labs; H-3403, Biocare Medical; 012215). To ensure optimal cellular contrast a bluing reagent was used with Hemotoxylin (Statlab, SL203). The slides were air dried and coverslipped with Biocare Ecomount (EM897L).

Image Acquisition and Analysis—Photomicrographs for immunohistochemistry were acquired with an Olympus BX51P polarizing microscope (DP71 Color Camera) and DP Controller software (Olympus, Verson 3.3.1.292). Images were quantitatively analysed using Image J (NIH). CD105+ MSCs were counted by an investigator blinded to the treatment group and sample identification. A random number generator was used to select 8 random image sets which were subsequently subjected to statistical analysis.

Statistical analyses—All data were analyzed with SIGMAPLOT® 12.5 software for statistical significance and are reported as mean±SEM. One-way ANOVA and the Holm-Sidak method for multiple comparisons were used to evaluate differences in histological measurements. Significance levels of P<0.001 are denoted in graphs by a triple asterisk ***. Representative results from at least three independent biological replicates are shown unless stated otherwise. (See FIGS. 25B and 25D)

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

REFERENCES

The following references, to the extent that they provide exemplary procedural or other details supplementary to those set forth herein, are specifically incorporated herein by reference.

International Publication No. WO98/30679

Wagner et al., Optimizing mesenchymal stem cell-based therapeutics. Curr Opin Biotechnol 20(5): 531-536, 2009.

We claim:

1. A cell preparation system comprising:
    a base; and
    a plurality of modular cell preparation apparatus coupled to the base, wherein each modular cell preparation apparatus comprises:
        an inlet fluid feed plate;
        a base plate;
        a first conduit;
        a second conduit;
        a plurality of intermediate plates positioned between the inlet fluid feed plate and the base plate;
        a reservoir; and
        a pump, wherein:
    the inlet fluid feed plate comprises a first fluid inlet, a first fluid outlet, a second fluid inlet and a second fluid outlet;
    the reservoir is coupled to the first fluid inlet via the first conduit; and
    the reservoir is coupled to the second fluid outlet via the second conduit.

2. The cell preparation system of claim 1 wherein the plurality of modular cell preparation apparatus comprises at least three modular cell preparation apparatus.

3. The cell preparation system of claim 1 wherein during use the plurality of modular cell preparation apparatus are configured to operate in parallel to prepare cells.

4. The cell preparation system of claim 1 wherein the plurality of intermediate plates comprises at least three intermediate plates.

5. The cell preparation system of claim 1 wherein each of the intermediate plates in the plurality of intermediate plates comprises:
    a first end, a second end, a first side, and a second side;
    a distribution channel proximal to the first end; and
    a gathering channel proximal to the second end, wherein:
        the distribution channel extends between the first side and the second side of the intermediate plate; and
        the gathering channel extends between the first side and the second side of the intermediate plate.

6. The cell preparation system of claim 5 wherein:
    the distribution channel of each intermediate plate has a first length;
    the gathering channel of each intermediate plate has a second length;
    each of the intermediate plates has a width between first side and a second side;
    the first length of the distribution channel extends across a majority of the width of the intermediate plate; and
    the second length of the gathering channel extends across a majority of the width of the intermediate plate.

7. The cell preparation system of claim 5 wherein:
    the distribution channel of each intermediate plate has a first length;
    the gathering channel of each intermediate plate has a second length;
    each of the intermediate plates has a width between first side and a second side;
    the first length of the distribution channel extends across at least 70 percent of the width of the intermediate plate; and
    the second length of the gathering channel extends across at least 70 percent of the width of the intermediate plate.

8. The cell preparation system of claim 1 wherein the pump of each modular cell preparation apparatus is coupled to the first fluid outlet and the second fluid inlet of the inlet fluid feed plate.

9. The cell preparation system of claim 1 wherein the pump comprises: a rolling element; and a flexible conduit, wherein the flexible conduit is coupled to the first fluid outlet and the second fluid inlet of the inlet fluid feed plate.

10. The cell preparation system of claim 9 further comprising an electric motor coupled to the rolling element.

11. The cell preparation system of claim 10 wherein a velocity of the fluid through the second fluid inlet is controlled by a rotational speed of the rolling element of the pump.

12. The cell preparation system of claim 9 wherein during use the pump is configured to:
    draw a fluid from the reservoir through first fluid inlet and the first fluid outlet; direct the fluid through the second fluid inlet, across the plurality of intermediate plates, out the second outlet, and back to the reservoir.

* * * * *